(12) United States Patent
Bruening et al.

(10) Patent No.: US 8,748,630 B2
(45) Date of Patent: Jun. 10, 2014

(54) PROCESS FOR PREPARING 2-AMINO-5-CYANOBENZOIC ACID DERIVATIVES

(75) Inventors: Joerg Bruening, Wilmington, DE (US); Albert Loren Casalnuovo, Wilmington, DE (US); Vladimir Grushin, Hockessin, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 893 days.

(21) Appl. No.: 12/517,429

(22) PCT Filed: Dec. 5, 2007

(86) PCT No.: PCT/US2007/025005
§ 371 (c)(1),
(2), (4) Date: Jun. 3, 2009

(87) PCT Pub. No.: WO2008/070158
PCT Pub. Date: Jun. 12, 2008

(65) Prior Publication Data
US 2010/0022780 A1 Jan. 28, 2010

Related U.S. Application Data

(60) Provisional application No. 60/873,058, filed on Dec. 6, 2006.

(51) Int. Cl.
C07C 253/14 (2006.01)
C07D 231/14 (2006.01)
C07D 231/16 (2006.01)
C07D 231/22 (2006.01)
C07D 401/04 (2006.01)

(52) U.S. Cl.
USPC ........................................ 548/374.1

(58) Field of Classification Search
None
See application file for complete search history.

(56) References Cited

U.S. PATENT DOCUMENTS 6,331,628 B1 12/2001 Kondo et al.
6,784,308 B2 8/2004 Eckert

FOREIGN PATENT DOCUMENTS

| JP | 2000344732 A | 12/2000 |
| JP | 2003064040 A | 3/2003 |
| WO | 2004/067528 A1 | 8/2004 |
| WO | 2006/023783 A1 | 3/2006 |
| WO | 2006/062978 A1 | 6/2006 |
| WO | 2006/068669 A1 | 6/2006 |

OTHER PUBLICATIONS

Schareina et al., Journal of Organometallic Chemistry, 689, 2004, 4576-4583.*

P. E. Maligres et al., "A Highly Catalytic Robust Palladium Catalyzed Cyanation of Aryl Bromides", Tetrahedron Lett. 1999, vol. 40, pp. 8193-8195.
M. Sundermeier et al., "Progress in the Palladium Catalyzed Cyanation of Aryl Chlorides", Chem. Eur. J. 2003, vol. 9, pp. 1828-1836.

(Continued)

Primary Examiner — Sun Jae Yoo
(74) Attorney, Agent, or Firm — Renee M. Lett

(57) ABSTRACT

Disclosed is a method for preparing a compound of Formula 1 comprising contacting a compound of Formula 2 with at least one compound of Formula 3 in the presence of a solvent comprising one or more organic solvents selected from ethers and nitriles and a catalytically effective amount of a palladium complex comprising at least one tertiary phosphine ligand of Formula 4

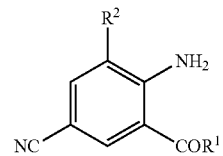

1

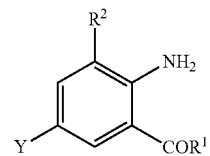

2

$M^1CN$

3

$P(R^5)(R^6)R^7$

4 wherein $R^1$ is $NHR^3$ or $OR^4$; $R^2$ is $CH_3$ or Cl; $R^3$ is H, alkyl, cyclopropyl, cyclopropylmethyl or methylcyclopropyl; $R^4$ is H or $C_1$-$C_4$ alkyl; $M^1$ is an alkali metal; and $R^5$, $R^6$ and $R^7$ are defined in the disclosure; provided that when $R^2$ is Cl, then X is Br. Also disclosed is a method for preparing a compound of Formula 5 wherein $R^{14}$, $R^{15}$, $R^{16}$ and Z are as defined in the disclosure using a compound of Formula 1 characterized by preparing the compound of Formula 1 by the aforedescribed method.

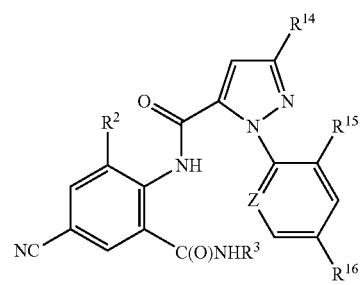

5

19 Claims, No Drawings

(56) References Cited

OTHER PUBLICATIONS

A. Sekiya et al., "Facile Synthesis of Aryl Cyanides from Iodides Catalyzed by Palladium Triphenylphosphine Complex", Chemistry Letters 1975, pp. 277-278.

Ramnauth, J. et al., "The Room-Temperature Palladium Catalyzed Cyanation of Aryl Bromides and Iodides with Tri-t-butylphosphine as Ligand" Synlett 2003, No. 14, pp. 2237-2239.

* cited by examiner

PROCESS FOR PREPARING 2-AMINO-5-CYANOBENZOIC ACID DERIVATIVES

FIELD OF THE INVENTION

The present invention pertains to a method for the preparation of 3-substituted 2-amino-5-cyanobenzoic acid derivatives.

BACKGROUND OF THE INVENTION

Preparation of certain 2-amino-5-cyanobenzoic acids and their utility as intermediates for preparing corresponding insecticidal cyanoanthranilic diamides has been disclosed (see e.g., Scheme 9 in PCT Patent Publication WO 2004/067528; Scheme 9 and Example 2, Step A in PCT Patent Publication WO 2006/068669; and Scheme 15 and Example 6, Step B in PCT Patent Publication WO 2006/062978).

Maligres et al., *Tetrahedron Lett.* 1999, 40, 8193 discloses a method for aromatic cyanation via bromide replacement using a Pd catalyst and $Zn(CN)_2$. PCT Patent Publication WO 2006/062978 discloses in Example 6, Step B the preparation of 2-amino-5-cyano-N,3-dimethylbenzamide by palladium-catalyzed cyanation using $Zn(CN)_2$ in N,N-dimethylformamide (DMF) as solvent. Because DMF is a high boiling, water-soluble solvent, it is not easily recycled.

Furthermore, cyanation using an alkali metal cyanide, such as potassium or sodium cyanide, would be less costly and would simplify purification of the final product. These salts, however, are more likely to deactivate metal catalysts and also more sensitive to choice of catalysts and solvent. Therefore $Zn(CN)_2$ is the metal cyanide most commonly used for palladium-catalyzed cyanation. A literature report of using potassium cyanide instead is Sundermeier et al., *Chem. Eur. J.* 2003, 9 (8), 1828-36, which discloses the cyanation of certain chloroarenes with a Pd catalyst and KCN at high temperatures and in the presence of at least 20 mol % of an amine as co-catalyst.

A need remains for versatile cyanation methods that can perform both Cl and Br replacement to prepare 2-amino-5-cyanobenzoic acid derivatives, do not require high temperatures or reaction-promoting co-catalysts, use easily recycled solvents and use cyanation agents that do not contain heavy metals.

SUMMARY OF THE INVENTION

The present invention relates to a method for preparing a compound of Formula 1

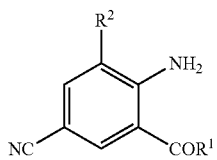

1 wherein
$R^1$ is $NHR^3$ or $OR^4$;
$R^2$ is Cl or $CH_3$;
$R^3$ is H, $C_1$-$C_4$ alkyl, cyclopropyl, cyclopropylmethyl or methylcyclopropyl; and
$R^4$ is H or $C_1$-$C_4$ alkyl;

comprising contacting (1) a compound of Formula 2

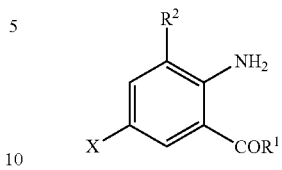

2 wherein X is Br or Cl;
with (2) at least one compound of Formula 3

$$M^1CN \qquad\qquad 3$$

wherein $M^1$ is an alkali metal
in the presence of (3) a solvent comprising one or more organic solvents selected from ethers and nitriles; and (4) a catalytically effective amount of a palladium complex comprising at least one tertiary phosphine ligand of Formula 4

$$P(R^5)(R^6)R^7 \qquad\qquad 4$$

wherein
$R^5$ is $C_3$-$C_{10}$ secondary alkyl, $C_4$-$C_{10}$ tertiary alkyl, neopentyl, $C_3$-$C_8$ cycloalkyl, phenyl or -L-$P(R^6)R^7$;
each $R^6$ and $R^7$ is independently tert-butyl, 1-adamantyl or phenyl; and
L is —$(CH_2)_3$—, —$(CH_2)_4$— or 1,1'-ferrocenediyl;
provided that when $R^2$ is Cl, then X is Br; and when X is Cl, then $R^5$, $R^6$ and $R^7$ are each tert-butyl.

This invention also provides a method for preparing a compound of Formula 5

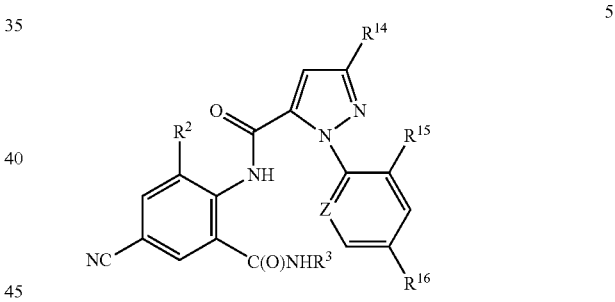

5 wherein
$R^2$ is Cl or $CH_3$;
$R^3$ is H, $C_1$-$C_4$ alkyl, cyclopropyl, cyclopropylmethyl or methylcyclopropyl;
Z is $CR^{17}$ or N;
$R^{14}$ is Cl, Br, $CF_3$, $OCF_2H$ or $OCH_2CF_3$;
$R^{15}$ is F, Cl or Br;
$R^{16}$ is H, F or Cl; and
$R^{17}$ is H, F, Cl or Br;
using a compound of Formula 1. The method is characterized by preparing the compound of Formula 1 from the compound of Formula 2 by the method disclosed above.

DETAILS OF THE INVENTION

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As used herein, the terms "method" and "process" are synonymous. For example, "method for preparing" means the same as "process for preparing". Also, in the context of describing a method or process, the term "contacting" is synonymous with the term "combining". The expression "at least one" means the same as "one or more".

In the above recitations, the term "alkyl" includes, for example, methyl, ethyl, n-propyl, i-propyl, or the different butyl isomers. Unless otherwise specified, "alkyl" may be straight chain or branched. "Secondary alkyl" refers to an alkyl group wherein the carbon atom connecting the alkyl group to the remainder of the molecule is bonded to two and only two other carbon atoms in the alkyl group. "Tertiary alkyl" refers to an alkyl group wherein the carbon atom connecting the alkyl group to the remainder of the molecule is bonded to three other carbon atoms in the alkyl group. Both secondary alkyl and tertiary alkyl groups may also be branched at carbon atoms besides the carbon atom connecting the group to the remainder of the molecule. "Cycloalkyl" includes, for example, cyclopropyl, cyclobutyl, cyclopentyl, cyclohexyl, cycloheptyl and cyclooctyl. As used herein, "Ph" is an abbreviation of phenyl.

Carbon-based radical refers to a monovalent molecular component comprising a carbon atom that connects the radical to the remainder of the chemical structure through a single bond. Carbon-based radicals can optionally comprise saturated, unsaturated and aromatic groups, chains, rings and ring systems, and heteroatoms. Although carbon-based radicals are not subject to any particular limit in size, in the context of the present invention they typically comprise 1 to 16 carbon atoms and 0 to 3 heteroatoms. Of note are carbon-based radicals selected from $C_1$-$C_4$ alkyl, $C_1$-$C_2$ haloalkyl and phenyl optionally substituted with 1-3 substituents selected from $C_1$-$C_3$ alkyl, halogen and nitro.

The term "monodentate" in reference to a tertiary phosphine of Formula 4 means the tertiary phosphine is a monodentate ligand (i.e. $R^5$ is other than -L-P($R^6$)$R^7$).

As referred to in the present disclosure, the term "carboxylic acid" means an organic chemical compound comprising at least one carboxylic acid functional group (i.e. —C(O)OH). The term "carboxylic acid" does not include the compound carbonic acid (i.e. HOC(O)OH). Carboxylic acids include, for example, formic acid, acetic acid, propionic acid, chloroacetic acid, benzoic acid, maleic acid, and citric acid. The term "effective $pK_a$" refers to the $pK_a$ of the carboxylic acid functional group, or if the compound has more than one carboxylic acid functional group, "effective $pK_a$" refers to the $pK_a$ of the most acidic carboxylic acid functional group. As referred to herein, the "effective pH" of a nonaqueous substance or mixture, such as a reaction mixture, is determined by mixing an aliquot of the substance or mixture with about 5 to 20 volumes of water and then measuring the pH of the resulting aqueous mixture (e.g., with a pH meter). As referred to herein, a "substantially anhydrous" substance means the substance contains no more than about 1% water by weight. The chemical name "isatoic anhydride" is another name corresponding to the current Chemical Abstracts name "2H-3,1-benzoxazine-2,4(1H)-dione".

In some instances herein ratios are recited as single numbers, which are relative to the number 1; for example, a ratio of 4 means 4:1.

Embodiments of the present invention include:

Embodiment A1

The method described in the Summary of the Invention for preparing a compound of Formula 1 comprising contacting reagent (1) (i.e. a compound of Formula 2) with reagent (2) (i.e. at least one compound of Formula 3) in the presence of reagent (3) (i.e. a solvent comprising one or more organic solvents selected from ethers and nitriles) and reagent (4) (i.e. a palladium complex comprising at least one tertiary phosphine ligand of Formula 4).

Embodiment A2

The method of Embodiment A1 wherein the palladium complex is generated in situ.

Embodiment A3

The method of Embodiment A1 wherein $R^5$ is tert-butyl.

Embodiment A4

The method of Embodiment A1 wherein each $R^6$ and $R^7$ is independently tert-butyl or 1-adamantyl.

Embodiment A5

The method of Embodiment A4 wherein each $R^6$ and $R^7$ is tert-butyl.

Embodiment A6

The method of Embodiment A1 wherein the palladium is complexed with at least one ligand selected from the group consisting of benzyl-di-1-adamantyl-phosphine, 1,1'-bis(diphenylphosphino)ferrocene, di-tert-butylneopentylphosphine and tri-tert-butylphosphine.

Embodiment A7

The method of Embodiment A1 wherein the solvent comprises one or more organic solvents selected from the group consisting of tetrahydrofuran, dioxane and acetonitrile.

Embodiment A8

The method of Embodiment A7 wherein the solvent comprises one or more organic solvents selected from the group consisting of tetrahydrofuran and dioxane.

Embodiment A9

The method of Embodiment A8 wherein the solvent comprises tetrahydrofuran.

Embodiment A10

The method of Embodiment A1 wherein the solvent comprises an ether.

Embodiment A11

The method of any one of Embodiments A8, A9 or A10 wherein the solvent further comprises a nitrile.

Embodiment A12

The method of Embodiment A11 wherein the solvent comprises acetonitrile.

Embodiment A13

The method of Embodiment A7 wherein the solvent is selected from the group consisting of tetrahydrofuran, dioxane and acetonitrile.

Embodiment A14

The method of Embodiment A7 wherein the solvent comprises one or more organic solvents selected from the group consisting of tetrahydrofuran and acetonitrile.

Embodiment A15

The method of any one of Embodiments A1 or A7 through A14 wherein the solvent further comprises a crown ether.

Embodiment A16

The method of Embodiment A1 wherein reagent (1), reagent (2), reagent (3) and reagent (4) are contacted at a temperature between about 0 and about 140° C.

Embodiment A17

The method of Embodiment A11 wherein reagent (1), reagent (2), reagent (3) and reagent (4) are contacted at a temperature between about 20 and about 100° C.

Embodiment A18

The method of Embodiment A1 wherein the method is performed at a temperature of 0 to 140° C.

Embodiment A19

The method of Embodiment A18 wherein the method is performed at a temperature of 20 to 100° C.

Embodiment A20

The method of Embodiment A1 wherein reagent (1), reagent (2), reagent (3) and reagent (4) are contacted at a temperature of at least about 0° C.

Embodiment A21

The method of Embodiment A20 wherein reagent (1), reagent (2), reagent (3) and reagent (4) are contacted at a temperature of at least about 20° C.

Embodiment A22

The method of Embodiment A1 wherein reagent (1), reagent (2), reagent (3) and reagent (4) are contacted at a temperature of not greater than about 140° C.

Embodiment A23

The method of Embodiment A22 wherein reagent (1), reagent (2), reagent (3) and reagent (4) are contacted at a temperature of not greater than about 100° C.

Embodiment A24

The method of Embodiment A1 wherein reagent (1), reagent (2), reagent (3) and reagent (4) are contacted in the presence of a catalyst promoter.

Embodiment A25

The method of Embodiment A1 wherein reagent (1), reagent (2), reagent (3) and reagent (4) are contacted in the presence of zinc metal.

Embodiment A26

The method of Embodiment A1 wherein the method is performed in the presence of zinc metal.

Embodiment A27

The method of Embodiment A25 or A26 wherein the zinc metal is in the form of zinc powder or dust.

Embodiment A28

The method of Embodiment A25, A26 or A27 wherein the zinc metal is activated.

Embodiment A29

The method of Embodiment A1 wherein reagent (1), reagent (2), reagent (3) and reagent (4) are contacted under an inert gas.

Embodiment A30

The method of Embodiment A1 wherein $R^1$ is $NHR^3$.

Embodiment A31

The method of Embodiment A1 wherein $R^3$ is $C_1$-$C_4$ alkyl or cyclopropylmethyl.

Embodiment A32

The method of Embodiment A31 wherein $R^3$ is methyl.

Embodiment A33

The method of Embodiment A1 wherein $R^2$ is methyl.

Embodiment A34

The method of Embodiment A1 wherein $M^1$ is Na or K.

Embodiment A35

The method of Embodiment A1 wherein reagent (2) is in the form of a powder.

Embodiment B1

The method described in the Summary of the Invention for preparing a compound of Formula 5 using a compound of Formula 1 prepared from the compound of Formula 2.

Embodiment B2

The method of Embodiment B1 wherein $R^1$ is $NHR^3$.

Embodiment B3

The method of Embodiment B1 wherein Z is N.

Embodiment B4

The method of Embodiment B1 wherein $R^3$ is $C_1$-$C_4$ alkyl or cyclopropylmethyl.

Embodiment B5

The method of Embodiment B4 wherein $R^3$ is methyl.

Embodiment B6

The method of Embodiment B1 wherein $R^2$ is methyl.

Embodiment B7

The method of Embodiment B1 wherein $R^{14}$ is Br.

Embodiment B8

The method of Embodiment B1 wherein $R^{15}$ is Cl.

Embodiment B9

The method of Embodiment B1 wherein $R^{16}$ is H.

Embodiment B10

The method of Embodiment B1 wherein Z is CH.

Embodiments of this invention can be combined in any manner.

In the following Schemes 1-8 the definitions of $R^1$, $R^2$, $R^3$, $R^4$, $R^{14}$, $R^{15}$, $R^{16}$, $R^{17}$, $M^1$, X and Z in the compounds of Formulae 1-12 are as defined above in the Summary of the Invention unless otherwise noted. Formulae 1a-1c are various subsets of Formula 1, and all substituents for Formulae 1a-1c are as defined above for Formula 1.

As shown in Scheme 1, in the method of the present invention a compound of Formula 1 is prepared by contacting a compound of Formula 2 with at least one alkali metal cyanide of Formula 3 in the presence of a solvent comprising one or more organic solvents selected from ethers and nitriles and a catalytically effective amount of a palladium complex comprising at least one tertiary phosphine ligand of Formula 4.

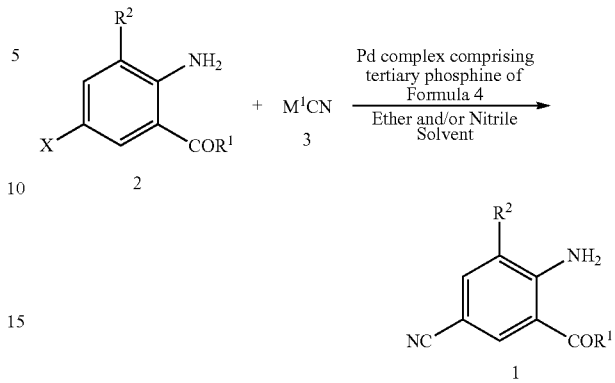

Scheme 1

In the method of Scheme 1, compounds of Formula 3 comprise $M^1$, which is an alkali metal, preferably K, Na, Cs or Rb, and most typically K or Na. The stoichiometry of the reaction requires at least one molar equivalent of cyanide provided by the compound or compounds of Formula 3. Although greater amounts of Formula 3 compounds can be used, there is no particular advantage in doing so, and greater amounts increase starting material and waste processing costs. Typically the molar ratio of the compound or compounds of Formula 3 (i.e. amount of CN) relative to the compound of Formula 2 is from about 1 to about 2, more typically from about 1 to about 1.5, and most typically from about 1 to about 1.3. In some cases the optimal molar ratio of Formula 3 cyanides to the compound of Formula 2 varies depending upon the particle size of the Formula 3 cyanides (although the molar ratios are still within the ratios described above). For example, commercially obtained alkali metal cyanides can consist of irregularly shaped particles with varying particle size distributions; thus the optimal molar ratio is sometimes greater when using commercially obtained alkali metal cyanides instead of using smaller particle size material. Grinding or milling alkali metal cyanides prior to use can provide smaller particle size material. Therefore in one embodiment of the present method the compounds of Formula 3 are used in the form of a powder. In some instances best results may be obtained from using an alkali metal cyanide that has not been ground to a powder before addition to the reaction mixture.

In the method of Scheme 1, the palladium complex catalyzes the cyanation of the compound of Formula 2 to form the compound of Formula 1, and therefore the palladium complex can be regarded as a palladium catalyst. As is well known to those skilled in the art, a palladium complex is a coordination compound wherein the palladium atom is bonded via coordinate covalent bonds to one or more ligands. Typically the palladium atom is in a formal 0 or +2 oxidation state, and indeed the oxidation state is believed to cycle between 0 and +2 during the course of the reaction.

Ligands and coordination chemistry are well known in the art, as is described in "Coordination Compounds", *Kirk-Othmer Encyclopedia of Chemical Technology*, John Wiley & Sons. DOl: 10.1002/0471238961.0315151801180308.a01.pub2. Ligands are typically Lewis bases having at least one pair of electrons available for coordination to the metal atom. Ligands in general can be neutral or charged, and can be unidentate, bidentate or higher. Ligands typically have at least one functional group comprising a nitrogen, oxygen, phosphorus, sulfur or arsenic atom with a free electron pair available for coordination to a metal atom.

For palladium-catalyzed cyanation of compounds of Formula 2 to Formula 1 in ether and nitrile solvents according to the present invention, certain tertiary phosphines have been discovered to work particularly well as ligands in the palladium complexes providing catalysis. These tertiary phosphines are generically described by Formula 4.

$$P(R^5)(R^6)R^7 \quad\quad 4$$

wherein
$R^5$ is $C_3$-$C_{10}$ secondary alkyl, $C_4$-$C_{10}$ tertiary alkyl, neopentyl, $C_3$-$C_8$ cycloalkyl, phenyl or -L-P($R^6$)$R^7$;
each $R^6$ and $R^7$ is independently tert-butyl, 1-adamantyl or phenyl; and
L is —(CH$_2$)$_3$—, —(CH$_2$)$_4$— or 1,1'-ferrocenediyl.

Examples of these tertiary phosphines include triphenylphosphine, tris(1,1-dimethyl-ethyl)phosphine (also named tri-tert-butylphosphine), bis(1,1-dimethylethyl)(2,2-dimethylpropyl)phosphine (also named di-tert-butylneopentylphosphine), cyclohexylbis(1,1-dimethylethyl)phosphine (also named di-tert-butylcyclohexylphosphine), bis(1,1-dimethylethyl)phenylphosphine (also named di-tert-butylphenylphosphine), bis(1,1-dimethylethyl)(1-methylethyl)phosphine (also named di-tert-butylisopropylphosphine), 1,1'-(1,4-butanediyl)bis[1,1-diphenylphosphine] (also named 1,4-bis(diphenylphosphino)butane), 1,1'-(1,3-propanediyl)bis[1,1-diphenylphosphine] (also named 1,3-bis(diphenylphosphino)-propane), 1,1'-bis(diphenylphosphino) ferrocene (abbreviated dppf or DPPF) and (phenyl-methyl) bis(tricyclo[3.3.1.13.7]dec-1-yl)phosphine (also named benzyl-di-1-adamantyl-phosphine).

Furthermore, tert-butyl has been discovered to be a phosphorus substituent providing palladium complexes with the greatest catalytic effectiveness for the present method. Therefore preferred are tertiary phosphine ligands wherein at least one of $R^5$, $R^6$ and $R^7$, and more preferably at least two of $R^5$, $R^6$ and $R^7$ are tert-butyl. Most preferably, each of $R^5$, $R^6$ and $R^7$ are tert-butyl (i.e. tri-tert-butylphosphine). Because compounds of Formula 2 wherein X is Cl instead of Br are much less reactive to cyanation, tri-tert-butylphosphine is the only tertiary phosphine ligand recommended for the present method when X is Cl.

The palladium complex according to the present method must comprise at least one tertiary phosphine ligand of Formula 4 and may further comprise other ligands as well. The palladium complex comprising at least one tertiary phosphine ligand of Formula 4 can be added to the reaction medium containing the compounds of Formulae 2 and 3 and the solvent, or the palladium complex can be formed in situ. The palladium complex is readily prepared in situ by simply contacting a palladium source with the tertiary phosphine ligand of Formula 4 in the reaction medium. Although finely divided palladium metal can provide a source of palladium, more typically the palladium source is a palladium salt or complex. Examples of palladium salts include, but are not limited to, halides such as chlorides, nitrates, sulfates, acetates or mixtures thereof. Although a wide range of palladium complexes can be used as palladium sources, the commercially available complex tris(dibenzylideneacetone)dipalladium(0) (Pd$_2$(dba)$_3$) has been found to be particularly convenient and useful for in situ formation of palladium complexes comprising at least one tertiary phosphine ligand of Formula 4. Although tertiary phosphine ligands of Formula 4 can be added to the reaction medium in the form of the unprotonated phosphines, often they are more readily available and handled as phosphonium salts, such as tetrafluoroborates. The unprotonated phosphines can be liberated from the phosphonium salts by contact with a base in the presence of the solvent comprising at least one organic solvent selected from ethers and nitriles. A wide variety bases can be used, including alkoxides such as potassium tert-butoxide and alkali metal carbonates such as sodium carbonate.

Palladium complexes comprising at least one tertiary phosphine ligand of Formula 4 have been discovered to be very effective catalysts for cyanation of compounds of Formula 2 to compounds of Formula 1 using alkali metal cyanides in ether and nitrile solvents. Accordingly, a catalytically effective amount of the palladium complex in the method of Scheme 1 can be quite small and yet still achieve significant conversion. The inclusion of catalyst promoters such as zinc metal can allow reducing the amount of palladium complex while retaining useful conversions. Typically the palladium complex is used in an amount of at least about 0.01 mol % Pd relative to the compound of Formula 2. More typically the palladium complex is used in an amount of at least about 0.1 mol % Pd relative to the compound of Formula 2. The upper limit on the amount of amount palladium complex is set primarily by economic considerations, but typically the amount of palladium complex does not exceed about 5 mol % Pd relative to the compound of Formula 2, and more typically the amount does not exceed about 2 mol %. The optimum amount of palladium complex for a desired rate of conversion and choice of tertiary phosphine, alkali metal cyanide, solvent and other process conditions can be determined by simple experimentation. An amount of palladium complex of about 1 mol % Pd relative to the compound of Formula 2 may be a convenient starting point.

A wide range of molar ratios of the one or more tertiary phosphines of Formula 4 to palladium can be used in the method of Scheme 1, but typically the ratio of total moles of phosphine to palladium is from about 0.5:1 to about 5:1. More typically the ratio of total moles for phosphine to palladium is from about 0.8:1 to about 3:1. Ratios of about 1:1 total moles of monodentate tertiary phosphines to palladium typically provide optimal catalytic activity for cyanation according to the method of Scheme 1 at temperatures up to about 85° C., while ratios of about 2:1 provide increased catalyst stability at higher temperatures. Often about a 1:1 molar ratio is used in the present method wherein in the compound of Formula 2, X is Br, which allows the cyanation to proceed at conveniently rapid rates at temperatures below about 85° C., while about a 2:1 molar ratio of monodentate tertiary phosphine to palladium is used with a compound of Formula 2 wherein X is Cl, which typically requires temperatures above about 85° C. for conveniently rapid reaction rates. Optimal molar ratios of phosphine to palladium can be determined by simple experimentation.

The present method can be performed in the presence of one or more catalyst promoters. Catalyst promoters are typically reducing agents such as metallic zinc and manganese, including alloys comprising them (e.g., manganese-iron alloy), and silane reducing agents (e.g., polymethylhydrosiloxane). Zinc metal has been found to be particularly useful in the present method. To provide greatest surface area, zinc metal in the reaction medium is typically in the form of a powder or dust (e.g., particle diameter<10 μm). The zinc metal can be activated by treatment with aqueous acid to remove oxide coating on the zinc metal particles before adding to the reaction medium. However, zinc metal powder or dust can also be used without prior activation. Catalyst promoters such as zinc metal are optional in the present method, but because catalyst promoters can allow decreasing the amount of palladium complex while retaining good conversions, including a catalyst promoter such as zinc metal in the reaction medium is an embodiment of particular note. Particularly because zinc metal is optional and an large excess is not deleterious, a very wide range of molar ratios of zinc to palladium can be used. Typically the molar ratio of zinc to palladium ranges from about 5:1 to about 50:1, and more typically from about 10:1 to about 40:1. Typically the molar amount of zinc relative to the compound of Formula 2 ranges from about 1 mol % to about 50 mol %, and more typically from about 2 mol % to about 20 mol %.

The method of Scheme 1 is conducted in the presence of a solvent comprising at least one organic solvent selected from ethers and nitrites (including mixtures thereof). These solvents are relatively easily separated by distillation for recycling. As is well known to those skilled in the art, ether solvents are organic compounds comprising at least one ether (i.e. —O—) moiety joining typically lower alkyl or alkylene radicals. Examples of common ether solvents include diethyl ether, 1,2-dimethoxyethane (also known as glyme), diethylene glycol dimethyl ether (also known as diglyme), tetrahydrofuran and dioxane. Tetrahydrofuran and dioxane have been found to be particularly useful for the present method. Also as is well known to those skilled in the art, nitrile solvents are organic compounds comprising a nitrile (i.e. —CN) radical bonded to typically a lower alkyl radical. Examples of nitrile solvents include acetonitrile and propionitrile. Acetonitrile has been found to be particularly useful for the present method. Ether and nitrile solvents have been discovered to work well for the palladium-catalyzed cyanation of compounds of Formula 2 to compounds of Formula 1 using alkali metal cyanides (i.e. Formula 3), so that zinc cyanide is not needed. However, these solvents have also been discovered to work well with zinc cyanide even for cyanation of compounds of Formula 2 wherein X is Cl. Of note as solvents for the present method are tetrahydrofuran, dioxane or acetonitrile (including mixtures thereof), and of particular note are tetrahydrofuran or acetonitrile (including mixtures thereof).

The solvent in the present method typically contains little water. Commercially available anhydrous grade solvents can be used, or the solvents can be dried by using conventional drying methods such as storing over molecular sieves or distillation from drying agents such as calcium hydride, phosphorus pentoxide and benzophenone-sodium. Oxygen is believed to be deleterious to the present catalytic method, so solvents are preferably deoxygenated (i.e. dissolved oxygen removed) before use. Solvents can be deoxygenated as well as dried by distillation from a drying agent under an oxygen-free atmosphere (e.g., nitrogen or argon gas). Alternatively, solvents can be deoxygenated by sparging (i.e. bubbling) an inert gas such as nitrogen or argon. In another method, solvents are deoxygenated by subjecting them to vacuum and then restoring pressure with an atmosphere of an inert gas such as nitrogen or argon.

The reactants can be added in a variety of orders to form the reaction medium, but typically and preferably the palladium complex comprising at least one tertiary phosphine of Formula 4 is added last. Often the palladium complex is added in solution. It has been discovered that when the reaction solvent comprises a nitrile solvent such as acetonitrile (in which certain palladium complexes such as tris(dibenzylideneacetone)dipalladium(0) do not readily dissolve), good results are obtained by dissolving or forming the palladium complex in solution of an ether solvent such as tetrahydrofuran and then adding the palladium complex solution to the reaction medium comprising the nitrile solvent. Therefore a noteworthy embodiment of the method of Scheme 1 comprises contacting a solution of the palladium complex comprising at least one tertiary phosphine of Formula 4 in a solvent comprising an ether with a mixture comprising the compound of Formula 2, at least one compound of Formula 3 and a nitrile solvent.

In ether and nitrile solvents the starting compound of Formula 2 and the palladium catalyst are typically soluble, while alkali metal cyanides of Formula 3 have only slight solubility. Therefore the alkali metal cyanides are typically present in the reaction medium as a slurry. While the reaction is occurring, agitation should be used to properly maintain the slurry, which will slowly dissolve during the course of the reaction.

The concentration of reactants and catalyst in solvent can be varied, although it will be appreciated that the selectivities and yields of the product can vary as well. Typically the ratio of volume of solvent to the weight of starting compound of Formula 2 is at least about 3 mL/g, because more concentrated reaction mixtures can be difficult to stir. The reaction rate tends to decrease with increasing dilution and excess solvent increases cost, so typically the ratio of solvent volume to weight of starting compound of Formula 2 is no more than about 20 mL/g. More typically the ratio is at least about 4 mL/g and no more than about 15 mL/g.

Although phase transfer agents or solubilizers are typically not needed for the present method, phase transfer agents or solubilizers such as crown ethers (e.g., 18-crown-6) can be included in the solvent and may be advantageous in some circumstances.

The method of Scheme 1 can be conducted over a wide range of temperatures, provided that the temperature is not so high as to result in decomposition of the reactants or products. The reaction of the present method is typically performed at a temperature of about 0 to about 140° C., and more typically from about 20 to about 100° C.

As oxygen is believed to be deleterious to the present catalytic method, preferably not only are deoxygenated solvents used, but an atmosphere of a gas inert to the reactants and products is maintained over the reaction medium. Typically the inert gas is nitrogen or argon.

The product of the present method (i.e. the compound of Formula 1) can be isolated by standard techniques known in the art, including filtration, extraction, evaporation and crystallization. As the compounds of Formula 1 are typically solids at ambient temperature, they are most easily isolated by filtration, optionally preceded by concentration of the reaction mixture and optionally followed by washing with water and/or an organic solvent (e.g., acetonitrile). Additionally, product can be isolated by concentrating the filtrate under reduced pressure, slurrying the resulting residue in a suitable organic solvent (e.g., acetonitrile), filtering and optionally washing with water and/or an organic solvent (e.g., acetonitrile). The solids can be further purified by recrystallization from an appropriate organic solvent (e.g., ethanol, methanol, acetonitrile)

Starting compounds of Formula 2 can be made by a variety of methods known in the art. According to one general method, compounds of Formula 2 can be prepared by halogenation of corresponding compounds of Formula 6 as shown in Scheme 2. The reaction can be carried out using a variety of halogenating agents known in the literature including bromine, chlorine, sulfuryl chloride, N-chlorosuccinimide (NCS), N-bromo-succinimide (NBS), and halogenating agents such as mixtures comprising hydrogen peroxide and a hydrogen halide. For leading references describing these methods, see PCT Patent Publications WO 2006/068669 (Scheme 11 and Example 1, Step E), WO 2003/015519 (Scheme 4 and Example 1, Step A), WO2006/062978

(Scheme 15; Example 2, Step A; Example 4, Step B and Example 5, Step B), and WO 2004/067528 (Scheme 11 and Example 1, Step A).

Scheme 2

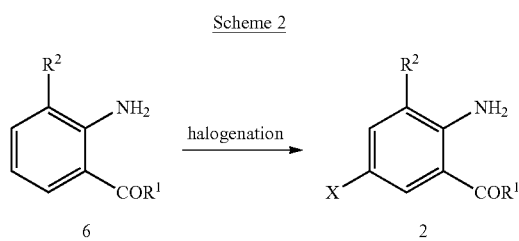

Another method for preparing compounds of Formula 2 (wherein X is Br and $R^1$ is $NHR^3$) involves bromination of compounds of Formula 6 by treatment with a gas containing bromine, as illustrated by the procedure of Reference Example 1.

Compounds of Formula 2 (wherein $R^1$ is $NHR^3$) can also be prepared by contacting an isatoic anhydride of Formula 7 with an alkyl amine of Formula 8 in the presence of a carboxylic acid as illustrated in Scheme 3.

Scheme 3

As amines such as the compound of Formula 8 are bases, in the absence of the carboxylic acid, the mixture of the compounds of Formulae 7 and 8 would be basic (i.e. effective pH>7). The carboxylic acid acts as a buffer to reduce the effective pH of the reaction mixture. A wide variety of carboxylic acids are useful, as the only requirement is for at least one carboxylic acid group to impart acidity. Other functional groups can be present, and more than one carboxylic acid group can be present on the carboxylic acid molecule. Typically the carboxylic acid has an effective $pK_a$ in the range of about 2 to about 5. Carboxylic acids include, for example, formic acid, acetic acid, propionic acid, chloroacetic acid, benzoic acid, phthalic acid, maleic acid, tartaric acid and citric acid. For reason of cost, inexpensive carboxylic acids such as formic acid, acetic acid, propionic acid and benzoic acid are preferred. Acetic acid, which is commercially available at low cost in its anhydrous form (known as "glacial acetic acid"), is particularly preferred.

The combination of the carboxylic acid with the basic amine of Formula 8 forms an amine salt of the carboxylic acid. This amine salt can be preformed before addition of the isatoic anhydride compound of Formula 7, or the amine salt can be generated in situ by metering the amine of Formula 8 into a mixture of the compound of Formula 7 and the carboxylic acid. For either mode of addition, maintaining the effective pH of the mixture during the reaction between about 3 and about 7 is generally optimal.

As the effective pH of the mixture results from the buffering effect of the carboxylic acid in combination with the amine of Formula 8, the effective pH can be adjusted according to the effective $pK_a$ of the carboxylic acid by adjusting the molar ratio of carboxylic acid to the amine of Formula 8. Typically the molar amounts of the amine of Formula 8 to carboxylic acid are in the range from about 0.8 to about 3. More particularly, when the mode of combination involves metering the amine of Formula 8 into a mixture of the isatoic anhydride compound of Formula 8 and carboxylic acid, the molar ratio of Formula 8 amine to carboxylic acid is preferably from about 0.95 to about 3. When the mode of combination involves forming the amine salt before addition of the compound of Formula 7 the molar ratio of Formula 8 amine to carboxylic acid is preferably from about 0.8 to about 1.05; as long as a nearly equimolar ratio (e.g. about 0.95 to about 1.05) of Formula 8 amine to carboxylic acid is used, the amine salt thus formed is typically used in a ratio of about 1.1 to about 5 molar equivalents relative to the compound of Formula 7. For optimal conversions, the molar ratio of amine of Formula 8 to isatoic anhydride compound of Formula 7 should be at least 1.0, although the molar ratio is preferred to be from about 1.1 to about 1.5 for reasons of efficiency and of economy, regardless of how the components are mixed. The molar amount of amine of Formula 8 relative to compound of Formula 7 can be substantially greater than 1.5, particularly when a nearly equimolar ratio (e.g., about 0.95 to about 1.05) of amine to acid is used.

Highest product yield and purity is achieved when the reaction medium is substantially anhydrous. The reaction medium is thus typically formed from substantially anhydrous compounds of Formula 7 and 8 and carboxylic acid. Preferably the reaction medium and forming materials contain about 5% or less, more preferably about 1% or less, and most preferably about 0.1% water or less (by weight). If the carboxylic acid is acetic acid, it is preferably in the form of glacial acetic acid.

The reaction of Scheme 3 is typically conducted in a liquid phase. In many cases the reaction can be carried out without solvent other than the compounds of Formulae 2, 7 and 8 and the carboxylic acid. But a preferred procedure involves use of a solvent that can suspend and at least partially dissolve the reactants. Preferred solvents are those which are non-reactive with the reaction components and have a dielectric constant of about 5 or greater, such as alkyl nitriles, esters, ethers, or ketones. Preferably the solvent should be substantially anhydrous to facilitate achieving a substantially anhydrous reaction medium. The weight ratio of solvent to the compound of Formula 7 is typically from about 1 to about 20, and preferably about 5 for reasons of efficiency and economy.

Carbon dioxide forms as a byproduct of the reaction of Scheme 3. Most of the carbon dioxide formed evolves from the reaction medium as a gas. The addition of the compound of Formula 7 into reaction medium containing the amine of Formula 8 or the addition of the amine of Formula 8 into the reaction medium containing the compound of Formula 7 is preferably conducted at such a rate and temperature as to facilitate controlling the evolution of carbon dioxide. The temperature of the reaction medium is typically between about 5 and 75° C., more typically between about 35 and 55° C.

The product of Formula 2 can be isolated by standard techniques known in the art, including pH adjustment, extraction, evaporation, crystallization and chromatography. For example, the reaction medium can be diluted with about 3 to 15 parts by weight of water relative to the starting compound of Formula 8, the pH can be optionally adjusted with either acid or base to optimize the removal of either acidic or basic impurities, the water phase can be optionally separated, and most of the organic solvent can be removed by distillation or evaporation at reduced pressure. As the compounds of Formula 2 are typically crystalline solids at ambient temperature, they are generally most easily isolated by filtration, optionally followed by washing with water and then drying.

As shown in Scheme 4, isatoic anhydrides of Formula 7 can be prepared from anthranilic acids of Formula 2a (Formula 2 wherein $R^1$ is $OR^4$ and $R^4$ is H) via a cyclization reaction involving treatment of the anthranilic acids with phosgene or a phosgene equivalent such as triphosgene or an alkyl chloroformate (e.g., methyl chloroformate) in a suitable solvent such as toluene or tetrahydrofuran. The method is described in PCT Patent Publication WO 2006/068669, including a specific example relevant to Scheme 4. Also see Coppola, *Synthesis* 1980, 505 and Fabis et al., *Tetrahedron* 1998, 10789.

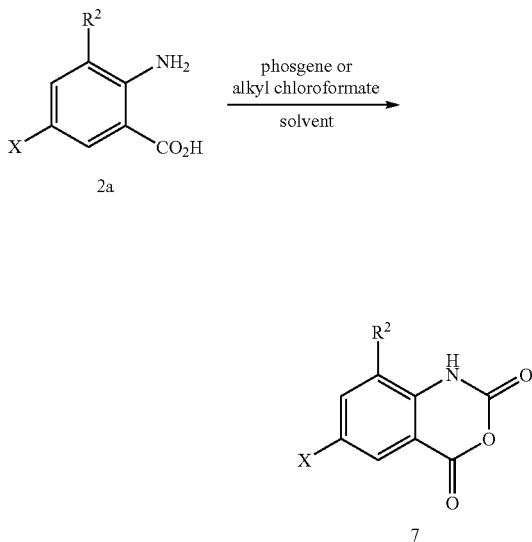

In another aspect of the present invention, compounds of the Formula 1 prepared by the method of Scheme 1 are useful as intermediates for preparing compounds of Formula 5. Compounds of Formula 5 are useful as insecticides, as described, for example in PCT Patent Publications WO 2003/015518 and WO 2006/055922.

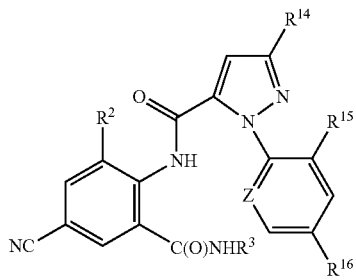

wherein $R^2$ is Cl or $CH_3$;

$R^3$ is H, $C_1$-$C_4$ alkyl, cyclopropyl, cyclopropylmethyl or methylcyclopropyl;

Z is $CR^{17}$ or N;

$R^{14}$ is Cl, Br, $CF_3$, $OCF_2H$ or $OCH_2CF_3$;

$R^{15}$ is F, Cl or Br;

$R^{16}$ is H, F or Cl; and $R^{17}$ is H, F, Cl or Br;

A variety of routes are possible for the preparation of a compound of Formula 5 from a compound of Formula 1. As outlined in Scheme 5, one such method involves the coupling of a compound of Formula 1a (Formula 1 wherein $R^1$ is $OR^4$ and $R^4$ is H) with a pyrazole-5-carboxylic acid of Formula 9, resulting in a cyanobenzoxazinone of Formula 10. Subsequent reaction of the cyanobenzoxazinone with an amine of Formula 11 provides a compound of Formula 5. Conditions for the first step involve sequential addition of methanesulfonyl chloride in the presence of a tertiary amine such as triethylamine or pyridine to a pyrazole of Formula 9, followed by the addition of a compound of Formula 1a, followed by a second addition of tertiary amine and methanesulfonyl chloride. The reaction can be run neat or in a variety of suitable solvents including tetrahydrofuran, diethyl ether, dioxane, toluene, dichloromethane or chloroform with optimum temperatures ranging from room temperature to the reflux temperature of the solvent. The second step, reaction of benzoxazinones with amines to produce anthranilamides, is well documented in the chemical literature. For a general review of benzoxazinone chemistry see Jakobsen et al., *Biorganic and Medicinal Chemistry* 2000, 8, 2095-2103 and references cited within, and G. M. Coppola, *J. Heterocyclic Chemistry* 1999, 36, 563-588. Also see PCT Patent Publication WO 2004/067528, which teaches the general method shown in Scheme 5, including experimental examples relevant to Scheme 5.

Scheme 5

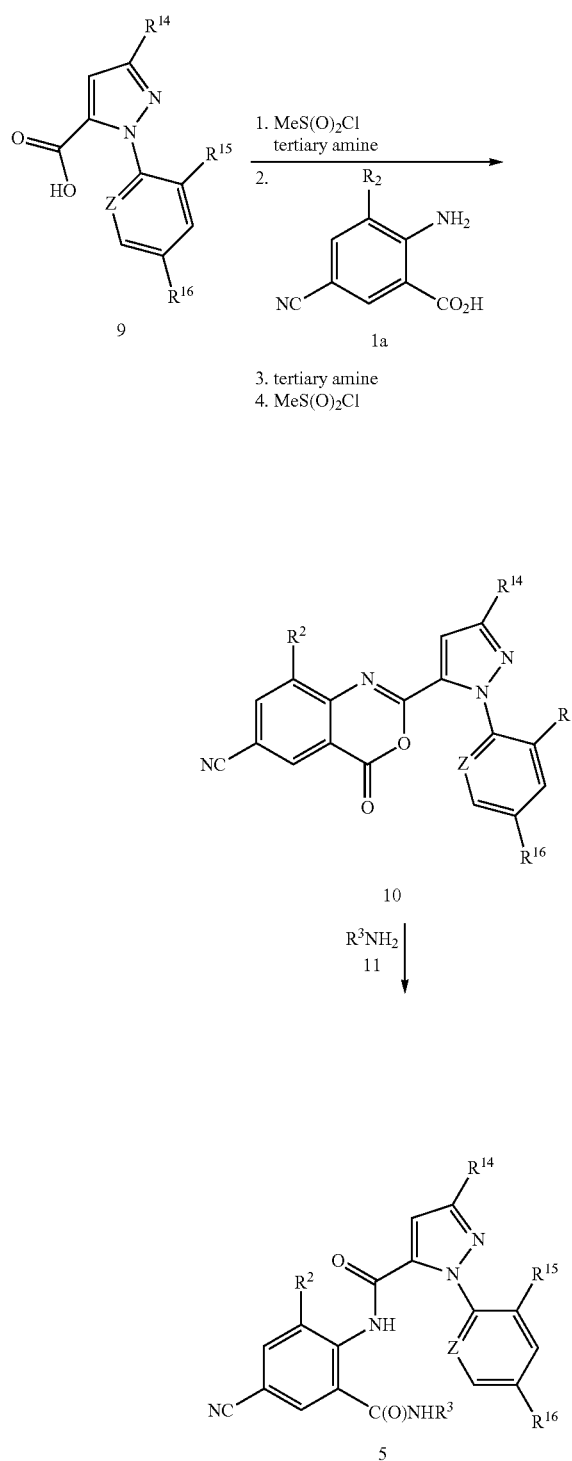

Another method of preparing compounds of Formula 5 is shown in Scheme 6. In this method a compound of Formula 5 is prepared by combining a compound of Formula 1b (Formula 1 wherein $R^1$ is $NHR^3$), a pyrazole of Formula 9 and sulfonyl chloride according to the general method taught in PCT Patent Publication WO 2006/062978, which is hereby incorporated herein in its entirety by reference.

Scheme 6

As described in WO 2006/062978 a variety of reaction conditions are possible for this transformation. Typically a sulfonyl chloride is added to a mixture of the compounds of Formulae 1b and 9 in the presence of a solvent and a base. Sulfonyl chlorides are generally of the formula $RS(O)_2Cl$ wherein R is a carbon-based radical. Usually for this method R is $C_1$-$C_4$ alkyl, $C_1$-$C_2$ haloalkyl, or phenyl optionally substituted with 1-3 substituents independently selected from the group consisting of halogen, $C_1$-$C_3$ alkyl and nitro. Commercially available sulfonyl chlorides include methanesulfonyl chloride (R is $CH_3$), propanesulfonyl chloride (R is $(CH_2)_2CH_3$), benzenesulfonyl chloride (R is phenyl), and p-toluenesulfonyl chloride (R is 4-methylphenyl). Methanesulfonyl chloride is of note for reasons of lower cost, ease of addition and/or less waste. At least one molar equivalent of the sulfonyl chloride per mole of the compound of Formula 9 is stoichiometrically needed for complete conversion. Typically the molar ratio of sulfonyl chloride to the compound of Formula 9 is no more than about 2.5, more typically no more than about 1.4.

The compound of Formula 5 is formed when the starting compounds of Formulae 1b, 9 and the sulfonyl chloride are contacted with each other in a combined liquid phase, in which each is at least partially soluble. Since the starting materials of Formulae 1b and 9 are typically solids at ordinary ambient temperatures, the method is most satisfactorily conducted using a solvent in which the starting compounds have significant solubility. Thus typically the method is conducted in a liquid phase comprising a solvent. In some cases the carboxylic acid of Formula 9 may have only slight solubility, but its salt with added base may have more solubility in the solvent. Suitable solvents for this method include nitriles such as acetonitrile and propionitrile; esters such as methyl acetate, ethyl acetate, and butyl acetate; ketones such as acetone, methyl ethyl ketone (MEK), and methyl butyl ketone; haloalkanes such as dichloromethane and trichloromethane; ethers such as ethyl ether, methyl tert-butyl ether, tetrahydrofuran (THF), and p-dioxane; aromatic hydrocarbons such as benzene, toluene, chlorobenzene, and dichlorobenzene; tertiary amines such as trialkylamines, dialkylanilines, and optionally substituted pyridines; and mixtures of the foregoing. Solvents of note include acetonitrile, propionitrile, ethyl acetate, acetone, MEK, dichloromethane, methyl tert-butyl ether, THF, p-dioxane, toluene, and chlorobenzene. Of particular note as the solvent is acetonitrile, as it often provides products in superior yield and/or purity.

As the reaction of the present method generates hydrogen chloride as a byproduct, which would otherwise bind to basic centers on the compounds of Formulae 1b, 5 and 9, the method is most satisfactorily conducted in the presence of at least one added base. The base can also facilitate constructive interaction of the carboxylic acid with the sulfonyl chloride compound and the anthranilamide. Reaction of an added base with the carboxylic acid of Formula 9 forms a salt, which may have greater solubility than the carboxylic acid in the reaction medium. Although the base may be added at the same time, in alternation, or even after the addition of the sulfonyl chloride, the base is typically added before the addition of the sulfonyl chloride. Some solvents such as tertiary amines also serve as bases, and when these are used as solvents they will be in large stoichiometric excess as bases. When the base is not used as the solvent the nominal mole ratio of the base to the sulfonyl chloride is typically from about 2.0 to about 2.2, and is preferably from about 2.1 to about 2.2. Preferred bases are tertiary amines, including substituted pyridines. More preferred bases include 2-picoline, 3-picoline, 2,6-lutidine, and pyridine. Of particular note as the base is 3-picoline, as its salts with carboxylic acids of Formula 9 are often highly soluble in solvents such as acetonitrile.

The compounds of Formula 5 can be isolated from the reaction mixtures by methods known to those skilled in the art, including crystallization, filtration and extraction. As disclosed in WO 2006/062978, in some cases under the coupling reaction conditions of Scheme 6 compounds of Formula 5, can partially cyclize to form iminobenzoxazine derivatives of Formula 12, as shown below in Scheme 7.

2006/062978 discloses specific examples relevant to the method of Scheme 6, including examples illustrating treatment of the reaction mixture with an aqueous acid solution prior to isolating compounds of Formula 5.

Alternatively, compounds of Formula 12 can be converted back to compounds of Formula 5 prior to isolation by contacting the reaction mixture with water and heating. Typically, the conversion of Formula 12 compounds to Formula 5 compounds can be achieved by adding between about 2 to 6 parts by weight of water relative to the weight of the starting compound of Formula 1 and then heating to between about 45 and about 65° C. The conversion of the compound of Formula 12 to the compound of Formula 5 is usually complete in 1 h or less.

Pyrazole-5-carboxylic acids of Formula 9 can be prepared from 5-oxo-3-pyrazolidinecarboxylates by treatment with a halogenating agent to give 3-halo-4,5-dihydro-1H-pyrazole-5-carboxylates, which can subsequently be treated with an oxidizing agent to provide esters of the acids of Formula 9. The esters can then be converted to the acids (i.e. Formula 9). Halogenating agents that can be used include, for example, phosphorous oxyhalides, phosphorous trihalides, phosphorous pentahalides, thionyl chloride, dihalotrialkylphosphoranes, dihalodiphenylphosphoranes, oxalyl chloride and phosgene. The oxidizing agents can be, for example, hydrogen peroxide, organic peroxides, potassium persulfate, sodium persulfate, ammonium persulfate, potassium monopersulfate (e.g., Oxone®) or potassium permanganate. See PCT Patent Publications WO 2003/016283, WO 2004/087689 and WO 2004/011453 for a description of the halogenation and oxidation methods, and a procedure for preparing the starting 5-oxo-3-pyrazolidinecarboxylates. To convert the esters to carboxylic acids a variety of methods reported in the chemical literature can be used, including nucleophilic cleavage under anhydrous conditions or hydrolysis involving the use of either acids or bases (see T. W. Greene and P. G. M. Wuts, *Protective Groups in Organic Synthesis*, 2nd ed., John Wiley & Sons, Inc., New York, 1991, pp. 224-269 for a review Scheme 7

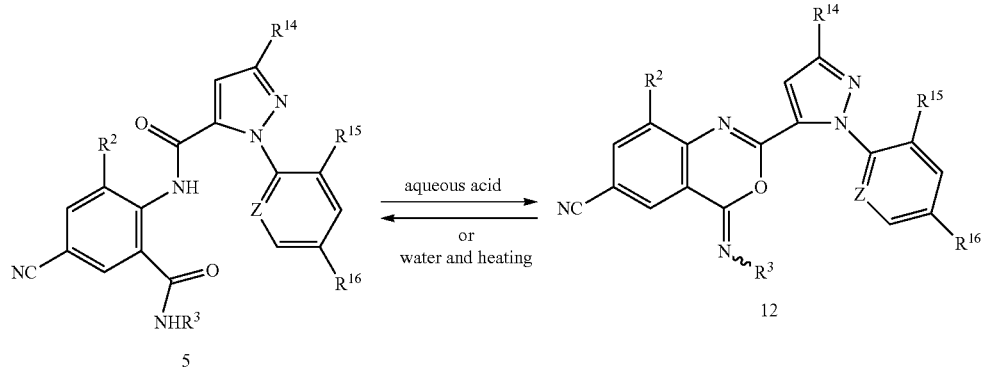

As discussed in WO 2006/062978, in these cases it is often advantageous to convert the iminobenzoxazine compounds of Formula 12 back to the amides of Formula 5 prior to isolation. This conversion can be accomplished by treatment of the reaction mixture with an aqueous acid solution (e.g., aqueous hydrochloric acid); or by isolating the mixture of Formula 12 and Formula 5 compounds, and then treating the mixture with an aqueous acid solution, optionally in the presence of a suitable organic solvent (e.g. acetonitrile). WO of methods). Base-catalyzed hydrolytic methods are preferred to prepare the carboxylic acids of Formula 9 from the corresponding esters. Suitable bases include alkali metal (such as lithium, sodium, or potassium) hydroxides. For example, the esters can be dissolved in a mixture of water and alcohol such as methanol. Upon treatment with sodium hydroxide or potassium hydroxide, the ester saponifies to provide the sodium or potassium salt of the carboxylic acid. Acidification with a strong acid, such as hydrochloric acid or sulfuric acid, gives the carboxylic acids. PCT Patent Publication WO 2003/016283 provides a relevant experimental example illustrating the base-catalyzed hydrolysis method for the conversion of an ester to an acid.

Alternatively, pyrazole-5-carboxylic acids of Formula 9 can be prepared from 4,5-dihydro-5-hydroxy-1H-pyrazole-5-carboxylates via an acid-catalyzed dehydration reaction to give the esters of Formula 9, which can then be converted to the acids. Typical reaction conditions involve treatment of 4,5-dihydro-5-hydroxy-1H-pyrazole-5-carboxylates with an acid, for example, sulfuric acid, in an organic solvent, such as acetic acid, at temperatures between about 0 and 100° C. The method is described PCT Patent Publication WO 2003/016282. Conversion of the esters to acids can be done using the methods described above. Also, WO 2003/016282 provides a relevant experimental example for the conversion of an ester to an acid.

Anthranilic amides of Formula 1b can also be prepared from the corresponding acids or esters of Formula 1c (Formula 1 wherein $R^1$ is $OR^4$ and $R^4$ is H or $C_1$-$C_4$ alkyl) as shown below in Scheme 8. Forming amides from carboxylic acids typically involves addition of a coupling agent (e.g., silicon tetrachloride, or alternatively dicyclohexylcarbodiimide or 1-ethyl-3-(3-dimethylaminopropyl)carbodiimide often in the presence of 1-hydroxy-benzotriazole). Preparation of anthranilic amides from anthranilic acids is disclosed in M. J. Kornet, *Journal of Heterocyclic Chemistry* 1992, 29(1), 103-5; PCT Publication WO 01/66519-A2; T. Asano et al., *Bioorganic & Medicinal Chemistry Letters* 2004, 14(9), 2299-2302; H. L. Birch et al. *Bioorganic & Medicinal Chemistry Letters* 2005, 15(23), 5335-5339; and D. Kim et al. *Bioorganic & Medicinal Chemistry Letters* 2005, 15(8), 2129-2134. Also T. Asano et al. reports preparation of an anthranilic amide from an anthranilic acid through an N-protected aniline intermediate or through a 4H-3,1-benzoxazine-2,4 (1H)-dione (isatoic anhydride) intermediate. Forming amides from esters often involves heating the ester with the appropriate amine in a polar solvent such as ethylene glycol. A procedure useful for conversion of anthranilic esters to anthranilic amides is described in PCT Patent Publication WO 2006/062978. Also, E. B. Skibo et al. *Journal of Medicinal Chemistry* 2002, 45(25), 5543-5555 discloses preparation of an anthranilic amide from the corresponding anthranilic ester using sodium cyanide catalyst.

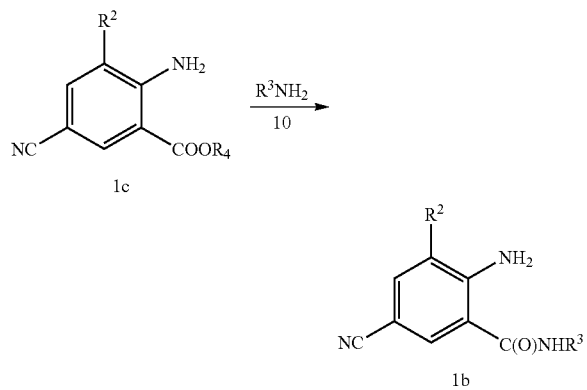

The methods of Schemes 5 and 6 are illustrative of just two of many methods for converting a compound of Formula 1 to a carboxamide of Formula 5. A wide variety of general methods are known in the art for preparing carboxamides from carboxylic acids and amines. For a general review, see M. North, *Contemporary Org. Synth.* 1995, 2, 269-287. Particular methods include contacting a compound of Formula 1b with a compound of Formula 9 in the presence of a dehydrating coupling agent such as 1,1'-carbonyldiimidazole, bis(2-oxo-3-oxazolidinyl)phosphinic chloride or benzotriazol-1-yloxy-tris(dimethylamino)-phosphonium hexafluorophosphate, or a polymer-bound analogous reagent such as polymer-bound dicyclohexylcarbodiimide, typically in an inert solvent such as dichloromethane or N,N-dimethylformamide, as is generally disclosed in PCT Patent Publication WO 2003/15518. Also disclosed in WO 2003/15518 is a method of preparing an acyl chloride derivative of the compound of Formula 9 by contacting Formula 9 compounds with thionyl chloride or oxalyl chloride in the presence of a catalytic amount of N,N-dimethylformamide, and then contacting the derived acyl chloride with the compound of Formula 1b in the presence of an acid scavenger, such as an amine base (e.g., triethylamine, N,N-diisopropylethylamine, pyridine, and polymer-supported analogs) or a hydroxide or carbonate (e.g., NaOH, KOH, $Na_2CO_3$, $K_2CO_3$), typically in an inert solvent such as tetrahydrofuran, 1,4-dioxane, ethyl ether or dichloromethane. The product, compounds of Formula 5, can be isolated from the reaction mixtures by methods known to those skilled in the ant, including crystallization, filtration and extraction.

Without further elaboration, it is believed that one skilled in the art using the preceding description can utilize the present invention to its fullest extent. The following Examples are, therefore, to be construed as merely illustrative, and not limiting of the disclosure in any way whatsoever.

EXPERIMENTAL EXAMPLES

The following Examples illustrate synthesis procedures, and the starting material of each Example may not have necessarily been prepared by a particular preparative run whose procedure is described in other Examples, including Reference Examples.

Zinc dust used in Examples 1 to 4, 11 and 13 was used as received from Aldrich. Activated zinc dust used in Examples 5 to 8 and 12 was prepared by stirring commercial zinc dust (J. T. Baker, 10 g) with 1 N hydrochloric acid (~20 mL) under nitrogen purge for 10 minutes, then collecting using vacuum filtration, successively washing with water (50 mL) and acetonitrile (50 mL), and drying in vacuo at ambient temperature. Activated zinc powder used in Examples 9 and 10 was prepared by stirring commercial zinc powder (J. T. Baker, 50 g) with 1 N hydrochloric acid (200 mL) for about 15 minutes, then collecting using vacuum filtration, successively washing with water (2×100 mL) and methanol (3×100 mL), and suction drying under nitrogen gas at ambient temperature.

As used in the present disclosure and claims, the term "deoxygenated" in relation to a solvent refers to removal of oxygen gas dissolved in the solvent. Tetrahydrofuran (THF) used in Examples 1 to 3 was dried and deoxygenated by distillation from sodium/benzophenone under nitrogen and stored over freshly calcined molecular sieves (4 Å) in a nitrogen-filled glovebox. Dioxane used in Examples 4 and 13 was anhydrous grade obtained from Aldrich and stored over molecular sieves. Tetrahydrofuran and acetonitrile used in Examples 5 to 8 and 12 was dried and deoxygenated by distillation from sodium/benzophenone and calcium hydride, respectively, under nitrogen. Acetonitrile used in Example 9 was anhydrous grade obtained from EMD Chemicals Inc., and was deoxygenated by three cycles of applying a vacuum (~330 Pa) followed by replenishment of the atmosphere with argon gas. Tetrahydrofuran used in Example 10 was anhydrous grade obtained from EMD Chemicals Inc., and was deoxygenated by four cycles of applying a vacuum (~330 Pa) followed by replenishment of the atmosphere with argon gas. Acetonitrile used in Example 11 was dried and deoxygenated by distillation from $P_2O_5$ under nitrogen.

PCT Patent Publication WO 2006/062978 describes procedures for preparing 2-amino-5-bromo-N,3-dimethylbenzamide and 2-amino-5-chloro-N,3-dimethylbenzamide. Reference Example 1 describes an additional procedure for preparing 2-amino-5-bromo-N,3-dimethylbenzamide. Both the 2-amino-5-bromo-N,3-dimethylbenzamide and 2-amino-5-chloro-N,3-dimethylbenzamide starting materials used in Examples 1 to 4 and 13 were purified using toluene solvent and a Soxhlet extractor fitted with two nested thimbles, in which the inner thimble contained the material to be purified, and the space between the inner and outer thimble contained silica gel, as described by Halliday, Young and Grushin. *Org. Lett.* 2003, 5, 2003-2005. This apparatus allowed simultaneous extraction, filtration through silica gel and crystallization of purified material.

The results from some of the Examples were analyzed by $^1$H NMR. Methods for preparation and $^1$H NMR spectra for the compounds analyzed have been previously reported. In particular, PCT Patent Publication WO 2006/062978 discloses preparation procedures and reference $^1$H NMR spectra for the following compounds: 2-amino-N,3-dimethylbenzamide-$^1$H NMR (CDCl$_3$) δ 2.14 (s, 3H), 2.94 (d, 3H, J=5 Hz), 5.37 (br s, 2H), 6.21 (br s, 1H), 6.56 (t, J=7.5 Hz, 1H), 7.10 (dd, J=7.5 Hz, 7.5 Hz, 1H), 7.18 (dd, J=7.5 Hz, 7.5 Hz, 1H); 2-amino-5-bromo-N,3-dimethylbenzamide-$^1$H NMR (CDCl$_3$) δ 2.14 (s, 3H), 2.95 (d, J=5 Hz, 3H), 5.55 (br s, 2H), 6.01 (br s, 1H), 7.21 (m, 1H), 7.30 (d, J=2 Hz, 1H); 2-amino-5-chloro-N,3-dimethylbenzamide-$^1$H NMR (DMSO-d$_6$) δ 2.08 (s, 3H), 2.72 (d, J=4.5 Hz, 3H), 6.34 (br s, 2H), 7.12 (d, J=2.4 Hz, 1H), 7.39 (d, J=2.4 Hz, 1H), 8.31 (br d, 1H); 2-amino-5-cyano-N,3-dimethylbenzamide-$^1$H NMR (CDCl$_3$) δ 2.16 (s, 3H), 2.98 (d, J=4.8 Hz, 3H), 6.17 (br s, 3H), 7.34 (d, J=1.8 Hz, 1H), 7.56 (d, J=1.8 Hz, 1H).

HPLC analysis in Examples 5 to 10 and 12 was performed using a Zorbax Eclipse XDB-C$_8$ reversed phase column (3.5 μm, 4.6×75 mm) eluted with a solvent gradient of acetonitrile in water with 0.1 volume % trifluoroacetic acid, and employing 254 nm UV detection.

In the following Examples, "mol %" is a molar comparison relative to the stalling compound of Formula 2. Similarly, "eq" relates to the number of equivalents relative to the starting compound of Formula 2. Selectivity as stated in Examples 4 and 13 refers to chemical reaction selectivity and is calculated by dividing the number of moles of desired product formed by the number of moles of starting material consumed, and then multiplying the quotient by 100%.

Reference Example 2 illustrates the method of Scheme 6, which is useful for preparing a compound of Formula 5 from a compound of Formula 1 prepared from a compound of Formula 2 by the method of Scheme 1.

Reference Example 1

Preparation of 2-amino-5-bromo-N,3-dimethylbenzamide (a compound of Formula 2)

A 1000-mL flask equipped with a mechanical stirrer, thermocouple, condenser and Teflon® fluoropolymer tubing (1/16" (0.16) cm I.D.×1/8" (0.32 cm) O.D.) (positioned such that the end of the tubing was submerged below the surface of the reaction mixture) was charged with acetic acid (226 mL). A solution of aqueous sodium hydroxide (50%, 25 g) in water (85 g) was added over 15 minutes, and then 2-amino-N,3-dimethylbenzamide (50 g, 0.305 mol) (see PCT Patent Publication WO 2006/062978 for a method of preparation) was added and the mixture was heated at 55° C. A two-necked 200-mL flask fitted on one neck with a Teflon® tubing dip tube was charged with liquid bromine (50.1 g), and the other neck was connected to the Teflon® tubing on the 1000-mL flask. Nitrogen gas was then flowed through the dip tube below the surface of the liquid bromine at a rate of about 0.012 m$^3$ (0.4 cu ft) per h for 2.5 h, during which time all of the bromine evaporated and the bromine vapor entrained in the nitrogen gas flowed out of the two-necked 200-mL flask and entered the reaction mixture through the Teflon® tubing. The reaction temperature was held at about 55° C. during the bromine vapor addition and for 30 minutes thereafter, and then cooled to 45° C. and stirred overnight. A solution of aqueous sodium hydroxide (50%, 52 g) in water (88 mL) was added to the reaction mixture at a rate of 0.8 mL/minute. After about 10% of the total volume of the sodium hydroxide solution had been added, the addition was stopped and the reaction mixture was stirred for 1 h at 45° C. After 1 h the remaining sodium hydroxide solution was added at a rate of 0.8 mL/minute. After the addition was complete, the reaction was stirred for 30 minutes at 45° C., and then cooled to 10° C. and stirred for 1 h. The mixture was filtered and the solid collected was washed with methanol (130 mL) and water (260 mL), and then dried to a constant weight in a vacuum-oven at 45° C. to give the title compound as a solid (67 g, 99.4 area % purity by HPLC, 89.7% yield) melting at 133-135° C.

$^1$H NMR (DMSO-d$_6$) δ 8.30 (m, 1H), 7.49 (d, 1H), 7.22 (d, 1H), 6.35 (br s, 2H), 2.70 (d, 3H), 2.06 (s, 3H).

Example 1

Preparation of 2-amino-5-cyano-N,3-dimethylbenzamide (a compound of Formula 1) from 2-amino-5-bromo-N,3-dimethylbenzamide (a compound of Formula 2) using NaCN, Pd$_2$(dba)$_3$, t-Bu$_3$P and zinc dust in THF In this example, reagents were transferred using a nitrogen-filled glovebox. A catalyst solution was prepared by stirring tris(dibenzylideneacetone)dipalladium(0) (Pd$_2$(dba)$_3$, Aldrich, 25 mg, 0.027 mmol, 0.055 mmol Pd) and tri-tert-butylphosphine (t-Bu$_3$P, Strem, 99%, 9 mg, 0.044 mmol) in THF (4 mL) at 25° C. for 1.5 h. In the glovebox, four standard 20-mL scintillation vials containing cylindrical Teflon®-coated 22×5 mm magnetic stirbars were charged for Experiments A, B, C and D as follows:

Experiment A. 2-amino-5-bromo-N,3-dimethylbenzamide (500 mg, 2.06 mmol), zinc (Zn) dust (Aldrich, 30 mg, 0.46 mmol), sodium cyanide (NaCN, Fluka, 97+%, ground with mortar and pestle in the glovebox, 130 mg, 2.65 mmol, 1.3 eq), THF (5 mL), and 1.5 mL of the catalyst solution (~1 mol % Pd, ~0.8 mol % P).

Experiment B. Same as Experiment A but the amount of Zn dust was reduced to 10 mg (0.15 mmol).

Experiment C. Same as Experiment A but the amount of the catalyst solution was reduced to 0.6 mL and 6 mL of THF was used.

Experiment D. Same as Experiment C but the amount of Zn dust was reduced to 10 mg (0.15 mmol).

The vials were sealed under nitrogen inside the drybox and the mixtures were vigorously stirred at 25° C. for 63 hours. Analysis of the reaction mixtures ($^1$H NMR) indicated the formation of the cyanated product 2-amino-5-cyano-N,3-dimethylbenzamide in >99% (Experiment A), >99% (Experiment B), 95% (Experiment C), and 83% (Experiment D) yield.

Example 2

Another preparation of 2-amino-5-cyano-N,3-dimethylbenzamide (a compound of Formula 1) from 2-amino-5-bromo-N,3-dimethylbenzamide (a compound of Formula 2) using NaCN, Pd$_2$(dba)$_3$, t-Bu$_3$P and zinc dust in THF In this example, reagents were transferred using a nitrogen-filled glovebox. A catalyst solution was prepared by dissolving Pd$_2$(dba)$_3$ (Aldrich, 36.2 mg, 0.040 mmol, 0.079 mmol Pd) and t-Bu$_3$P (Strem, 99%, 14.5 mg. 0.072 mmol) in THF (3 mL), then adding 2-amino-5-bromo-N,3-dimethylbenzamide (80 mg, 0.33 mmol), and stirring the mixture at 25° C. overnight. In the glovebox, a standard 20-mL scintillation vial containing a cylindrical Teflon®-coated 22×5 mm magnetic stirbar was charged with 2-amino-5-bromo-N,3-dimethylbenzamide (i.e. the product of Reference Example 1) (1.00 g, 4.11 mmol), Zn dust (Aldrich, 10 mg, 0.15 mmol, 3.6 mol %), NaCN (Fluka, 97+%, ground with a mortar and pestle in the glovebox, 215 mg, 4.39 mmol, 1.06 eq), THF (4 mL), and 0.32 mL of the catalyst solution (~0.19 mol % Pd, ~0.1.7 mol % P). The vial was sealed under nitrogen inside the drybox, and the mixture was vigorously stirred at 25° C. for 24 h. $^1$H NMR analysis of the reaction mixture indicated the formation of the cyanated product 2-amino-5-cyano-N,3-dimethylbenzamide in 95% yield.

Example 3

Another preparation of 2-amino-5-cyano-N,3-dimethylbenzamide (a compound of Formula 1) from 2-amino-5-bromo-N,3-dimethylbenzamide (a compound of Formula 2) using NaCN, Pd$_2$(dba)$_3$, t-Bu$_3$P and zinc dust in THF In this example, reagents were transferred using a nitrogen-filled glovebox. A catalyst solution was prepared by stirring Pd$_2$(dba)$_3$ (Aldrich, 38 mg, 0.041 mmol, 0.083 mmol Pd) and t-Bu$_3$P (Strem, 99%, 17 mg, 0.084 mmol) in THF (3 mL) at 25° C. for 3 h. In the glovebox, four standard 20-mL scintillation vials were charged for Experiments A, B, C and D as follows:

Experiment A. 1-amino-5-bromo-N,3-dimethylbenzamide (1.00 g, 4.11 mmol), Zn dust (Aldrich, 10 mg, 0.15 mmol, 3.6 mol %), NaCN (Fluka, 97+%, ground with a mortar and pestle in the glovebox, 210 mg, 4.28 mmol, 1.04 eq), THF (4 mL), and 0.3 mL of the catalyst solution (~0.2 mol % Pd, ~0.2 mol % P).

Experiment B. Same as Experiment A (reproducibility check).

Experiment C. Same as Experiment A but the amount of the catalyst solution was reduced to 0.15 mL (~0.1 mol % Pd, ~0.1 mol % P).

Experiment D. Same as Experiment C (reproducibility check).

The vials were sealed under nitrogen inside the drybox and the mixtures were sonicated in an Aquasonic 50HT ultrasonic bath at 25° C. for 24 h. $^1$H NMR analysis of the reaction mixtures indicated the formation of the cyanated product 2-amino-5-cyano-N,3-dimethylbenzamide in >99% (Experiment A), >99% (Experiment B), 95% (Experiment C), and 88% (Experiment D) yield.

Example 4

Preparation of 2-amino-5-cyano-N,3-dimethylbenzamide (a compound of Formula 1) from 2-amino-5-chloro-N,3-dimethylbenzamide (a compound of Formula 2) using KCN, (t-Bu$_3$P)$_2$Pd, zinc dust and 18-crown-6 in dioxane In this example, reagents were transferred using a nitrogen-filled glovebox. A mixture of 2-amino-5-chloro-N,3-dimethylbenzamide (1.00 g, 5.03 mmol), Zn dust (Aldrich, 15 mg, 0.23 mmol, 4.6 mol %), potassium cyanide (KCN, Aldrich, 97%, ground with a mortar and pestle in the glovebox, 0.33 g, 5.07 mmol, 1.0 eq), bis(tri-tert-butylphosphine)palladium(0) ((t-Bu$_3$P)$_2$Pd, prepared as described in *J. Am. Chem. Soc.* 2001, 123, 2719; 25 mg, 0.049 mmol, 0.97 mol % Pd), 18-crown-6 (Aldrich, 99.5+%, 15 mg, 0.057 mmol, 1.1 mol %) and dioxane (7 mL) in a Schlenk round-bottom flask was stirred under reflux and a nitrogen atmosphere for 24 h. $^1$H NMR analysis of the reaction mixture indicated the formation of 2-amino-5-cyano-N,3-dimethylbenzamide in 65% yield with >98% selectivity.

Example 5

Another preparation of 2-amino-5-cyano-N,3-dimethylbenzamide (a compound of Formula 1) from 2-amino-5-bromo-N,3-dimethylbenzamide (a compound of Formula 2) using NaCN, Pd$_2$(dba)$_3$, t-Bu$_3$P and zinc dust in acetonitrile and THF In this example, the reactions were carried out in a nitrogen-filled glovebox using standard glassware and magnetic stirring. A solution of Pd$_2$(dba)$_3$ (0.039 g, 0.040 mmol, 0.42 mol % Pd) and tri-tert-butylphosphine (0.018 g, 0.087 mmol, 0.43 mol % P) in tetrahydrofuran (5 mL) was stirred at ambient temperature for 30 minutes and then added to a mixture of 2-amino-5-bromo-N,3-dimethylbenzamide (5.00 g, 20.4 mmol), sodium cyanide (1.30 g, 25.7 mmol, 1.26 eq) and activated zinc dust (0.20 g, 3.1 mmol) in acetonitrile (35 mL). The green-brown heterogeneous mixture was stirred at 50° C. for 4.5 h, during which time the mixture became yellow-green and very thick with solids. Analysis by HPLC showed a 98:2 molar ratio of 2-amino-5-cyano-N,3-dimethylbenzamide to 2-amino-5-bromo-N,3-dimethylbenzamide, with a trace amount of the byproduct 2-amino-N,3-dimethylbenzamide.

Example 6

Preparation of 2-amino-5-cyano-N,3-dimethylbenzamide (a compound of Formula 1) from 2-amino-5-bromo-N,3-dimethylbenzamide (a compound of Formula 2) using NaCN, KO-t-Bu, t-Bu$_3$PH BF$_4$, Pd$_2$(dba)$_3$ and zinc dust in acetonitrile and THF In this example, the reactions were carried out in a nitrogen-filled glovebox using standard glassware and magnetic stirring. To prepare the catalyst solution a THF solution containing potassium tert-butoxide (1.0 M in THF; 0.10 mL, 0.10 mmol, 0.49 mol %) was combined with a solution of tri-tert-butylphosphonium tetrafluoroborate (Aldrich, 0.025 g, 0.084 mmol, 0.41 mol % P) in acetonitrile (1 mL), and the resulting mixture was stirred for 5 minutes at ambient temperature. To this mixture was added THF (4 mL) and $Pd_2(dba)_3$ (0.038 g, 0.040 mmol, 0.41 mol % Pd), and the resulting dark red mixture was stirred at ambient temperature. After 30 minutes, this catalyst solution was added to a mixture of 2-amino-5-bromo-N,3-dimethylbenzamide (5.00 g, 20.4 mmol), sodium cyanide (1.30 g, 25.7 mmol, 1.26 eq) and activated zinc dust (0.20 g, 3.1 mmol) in acetonitrile (35 mL) at ambient temperature. The green-brown heterogeneous mixture was stirred at 50° C. for 4.5 h, during which time the mixture became yellow-green and very thick with solids. Analysis by HPLC showed a 99:1 molar ratio of 2-amino-5-cyano-N,3-dimethylbenzamide to 2-amino-5-bromo-N,3-dimethylbenzamide, with a trace amount of the byproduct 2-amino-N,3-dimethylbenzamide.

Example 7

Preparation of 2-amino-5-cyano-N,3-dimethylbenzamide (a compound of Formula 1) from 2-amino-5-bromo-N,3-dimethylbenzamide (a compound of Formula 2) using NaCN, $Na_2CO_3$, $t$-$Bu_3$PH $BF_4$, $Pd_2(dba)_3$ and zinc dust in acetonitrile and THF In this example, the reactions were carried out in a nitrogen-filled glovebox using standard glassware and magnetic stirring. A mixture of sodium carbonate (0.109 g, 1.0 mmol, 5.0 mol %), $Pd_2(dba)_3$ (0.038 g, 0.040 mmol, 0.41 mol % Pd), and tri-tert-butylphosphonium tetrafluoroborate (Aldrich, 0.025 g, 0.084 mmol, 0.41 mol % P) in THF (5 mL) was stirred at ambient temperature. After 30 minutes, this catalyst mixture was added to a preheated mixture of 2-amino-5-bromo-N,3-dimethylbenzamide (5.00 g, 20.4 mmol), sodium cyanide (1.30 g, 25.7 mmol, 1.26 eq) and activated zinc dust (0.20 g, 3.1 mmol) in acetonitrile (35 mL) at 79° C. After the green slurry was stirred for 5 h at 79° C., the mixture was analyzed by HPLC. The HPLC analysis showed a 94:6 molar ratio of 2-amino-5-cyano-N,3-dimethylbenzamide to 2-amino-5-bromo-N,3-dimethylbenzamide, with about 0.8% of the byproduct 2-amino-N,3-dimethylbenzamide.

Example 8

Preparation of 2-amino-5-cyano-N,3-dimethylbenzamide (a compound of Formula 1) from 2-amino-5-bromo-N,3-dimethylbenzamide (a compound of Formula 2) using KCN, $Na_2CO_3$, $t$-$Bu_3$PH $BF_4$, $Pd_2(dba)_3$ and zinc dust in acetonitrile and THF In this example, the reactions were carried out in a nitrogen-filled glovebox using standard glassware and magnetic stirring. A mixture of sodium carbonate (0.109 g, 1.0 mmol, 5.0 mol %), $Pd_2(dba)_3$ (0.038 g, 0.040 mmol, 0.41 mol % Pd), and tri-tert-butylphosphonium tetrafluoroborate (Aldrich, 0.025 g, 0.084 mmol, 0.41 mol % P) in THF (5 mL) was stirred at ambient temperature. After 30 minutes, this catalyst mixture was added to a mixture of 2-amino-5-bromo-N,3-dimethylbenzamide (5.00 g, 20.4 mmol), potassium cyanide (1.30 g, 25.7 mmol, 1.26 eq) and activated zinc dust (0.20 g, 3.1 mmol) in acetonitrile (35 mL) at ambient temperature. After the slurry was stirred for 17 h at 50° C. the mixture was analyzed by HPLC. The HPLC analysis showed a 91:9 molar ratio of 2-amino-5-cyano-N,3-dimethylbenzamide to 2-amino-5-bromo-N,3-dimethylbenzamide, with a trace amount of the byproduct 2-amino-N,3-dimethylbenzamide.

Example 9

Preparation of 2-amino-5-cyano-N,3-dimethylbenzamide (a compound of Formula 1) from 2-amino-5-bromo-N,3-dimethylbenzamide (a compound of Formula 2) using NaCN, $Pd_2(dba)_3$, benzyl-di-1-adamantylphosphine, activated zinc powder in acetonitrile A slurry of 2-amino-5-bromo-N,3-dimethylbenzamide (5 g, 20.4 mmol), $Pd_2(dba)_3$ (Aldrich, 93 mg, 0.1 mmol, 1 mol % Pd), benzyl-di-1-adamantylphosphine (Strem, 94 mg, 0.2 mmol, 1 mol %), NaCN (ground under ambient atmosphere, 1.08 g, 21.4 mmol, 1.05 eq) and activated zinc powder (134 mg, 2.1 mmol, 10 mol %) in acetonitrile (40 mL) was heated to reflux (about 81-82° C.) while being stirred under nitrogen. The slurry was agitated for 17 h and sampled after dilution with N/N-dimethylformamide (40 mL). Analysis of the product mixture by HPLC showed 86% by area of 2-amino-5-cyano-N,3-dimethyl-benzamide.

Example 10

Preparation of 2-amino-5-cyano-N,3-dimethylbenzamide (a compound of Formula 1) from 2-amino-5-bromo-N,3-dimethylbenzamide (a compound of Formula 2) using NaCN, $Na_2CO_3$, $t$-$Bu_3$PH $BF_4$, $Pd_2(dba)_3$, activated zinc powder and water in THF A slurry of 2-amino-5-bromo-N,3-dimethylbenzamide (5 g, 20.4 mmol), $Pd_2(dba)_3$ (Aldrich, 37 mg, 0.040 mmol, 0.081 mmol Pd, 0.40 mol % Pd), tri-tert-butylphosphonium tetrafluoroborate (Strem, 25 mg, 0.084 mmol, 0.41 mol %), $Na_2CO_3$ (0.109 g, 1.0 mmol) and activated zinc powder (0.2 g, 3.1 mmol, 15 mol %) in THF (40 mL) was stirred for 30 min at ambient temperature, and then NaCN (1.3 g, 25.7 mmol, 1.26 eq) and water (0.1 g, 5.6 mmol) were added. The mixture was sampled after 2.5 h. Analysis by HPLC showed 21% by area of 2-amino-5-cyano-N,3-dimethylbenzamide.

Example 11

Preparation of 2-amino-5-cyano-N,3-dimethylbenzamide (a compound of Formula 1) from 2-amino-5-bromo-N,3-dimethylbenzamide (a compound of Formula 2) using KCN, (dppf)PdPh)(I), and zinc dust in acetonitrile In this example, reagents were transferred using a nitrogen-filled glovebox. A mixture of 2-amino-5-bromo-N,3-dimethylbenzamide (2.43 g, 10.0 mmol), Zn dust (Aldrich, 130 mg, 1.99 mmol), potassium cyanide (Aldrich, not ground, 0.73 g, 11.2 mmol, 1.12 eq), (dppf)Pd(Ph)(I) (prepared as described in *J. Am. Chem. Soc.* 1997, 119, 8232-45; 86 mg, 0.099 mmol, 0.99 mol % Pd) and acetonitrile (12 mL) in a Schlenk round-bottom flask was stirred under reflux and nitrogen atmosphere for 1 h 40 min. $^1$H NMR analysis of the reaction mixture indicated the formation of 2-amino-5-cyano-N,3-dimethylbenzamide in 40% yield.

Example 12

Preparation of 2-amino-5-cyano-N,3-dimethylbenzamide (a compound of Formula 1) from 2-amino-5-bromo-N,3-dimethylbenzamide (a compound of Formula 2) using NaCN, KO-t-Bu, $t$-$Bu_2$(neopentyl)PH $BF_4$, $Pd_2(dba)_3$ and zinc dust in acetonitrile and THF In this example, the reactions were carried out in a nitrogen-filled glovebox using standard glassware and magnetic stirring. To prepare the catalyst solution a THF solution of potassium tert-butoxide (1.0 M in THF; 0.10 mL, 0.10 mmol, 0.49 mol %) was combined with a solution of di-tert-butyl-neopentylphosphonium tetrafluoroborate (FMC Corp., 98%, 0.025 g, 0.081 mmol, 0.40 mol % P) in acetonitrile (1 mL), and the resulting mixture was stirred for 5 minutes at ambient temperature. To this mixture were added THF (4 mL) and $Pd_2(dba)_3$ (0.038 g, 0.040 mmol, 0.41 mol % Pd), and the resulting dark red mixture was stirred at ambient temperature. After 30 minutes, this catalyst solution was added to a mixture of 2-amino-5-bromo-N,3-dimethylbenzamide (5.00 g, 20.4 mmol), sodium cyanide (1.30 g, 25.7 mmol, 1.26 eq) and activated zinc dust (0.20 g, 3.1 mmol) in acetonitrile (35 mL) at ambient temperature. The green-brown heterogeneous mixture was stirred at 50° C. After 6 h, HPLC analysis showed a 36:64 molar ratio of 2-amino-5-cyano-N,3-dimethylbenzamide to 2-amino-5-bromo-N,3-dimethylbenzamide, with a trace amount of the byproduct 2-amino-N,3-dimethylbenzamide.

Example 13

Preparation of 2-amino-5-cyano-N,3-dimethylbenzamide (a compound of Formula 1) from 2-amino-5-chloro-N,3-dimethylbenzamide (a compound of Formula 2) using $Zn(CN)_2$, $(t-Bu_3P)_2Pd$ and zinc dust in dioxane In this example, reagents were transferred using a nitrogen-filled glovebox. A mixture of 2-amino-5-chloro-N,3-dimethylbenzamide (1.00 g, 5.03 mmol), Zn dust (Aldrich, 60 mg, 0.92 mmol), zinc cyanide ($Zn(CN)_2$, Aldrich, 98%, 0.32 g, 2.73 mmol, 1.08 eq), $(t-Bu_3P)_2Pd$ (prepared as described in *J. Am. Chem. Soc.* 2001, 123, 2719; 25 mg, 0.049 mmol, 0.97 mol % Pd) and dioxane (Aldrich, anhydrous, stored over molecular sieves, 8 mL) in a Schlenk round-bottom flask was stirred under reflux and nitrogen atmosphere for 11 h. $^1$H NMR analysis of the reaction mixture indicated the formation of 2-amino-5-cyano-N,3-dimethylbenzamide in 83% yield with >98% selectivity. This example illustrates that ether solvents such as dioxane are particularly useful with also zinc cyanide for cyanation of the less reactive compounds of Formula 2 wherein X is Cl.

Reference Example 2

Preparation of 3-bromo-1-(3-chloro-2-pyridinyl)-N-[4-cyano-2-methyl-6-[(methylamino)-carbonyl]phenyl]-1H-pyrazole-5-carboxamide (a compound of Formula 5)

To a mixture of 3-bromo-1-(3-chloro-2-pyridinyl)-1H-pyrazole-5-carboxylic acid (see PCT Patent Publication WO 2003/015519 for a method of preparation) (97.4% purity, 15.4 g, 49.6 mmol) and 2-amino-5-cyano-N,3-dimethylbenzamide (10.0 g, 52.5 mmol) in acetonitrile (80 mL) was added 3-picoline (13.9 g, 148 mmol). The mixture was cooled to 15 to 20° C., and then methanesulfonyl chloride (8.2 g, 71.2 mmol) was added dropwise at 15 to 20° C. After 1 h, water (37.3 g) was added dropwise to the reaction mixture while maintaining the temperature at 15 to 20° C. After the addition was complete, the mixture was heated at 45 to 50° C. for 30 minutes, and then cooled to 15 to 25° C. for 1 h. The mixture was filtered and the solids collected were washed with acetonitrile-water (approximately a 5:1 mixture, 2×10 mL) and acetonitrile (2×10 mL), and then dried under nitrogen to afford 24.0 g (93.6% corrected yield based on an assay of 91.6%, with a water content of 6%) of the title compound as an off-white solid.

$^1$H NMR (DMSO-$d_6$) δ 10.53 (br s, 1H) 8.49 (dd, 1H), 8.36 (m, 1H), 8.16 (dd, 1H), 7.87 (d, 1H), 7.76 (d, 1H), 7.60 (m, 1H), 7.41 (s, 1H), 2.67 (d, 3H), 2.21 (s, 3H).

Table 1 illustrates particular transformations to prepare compounds of Formula 1 from compounds of Formula 2 according to the method of the present invention. In particular, the conversion of a compound of Formula 2 to a compound of Formula 1 can be accomplished according to the method of Scheme 1. For these transformations, for example, the palladium complex comprises palladium(0) and tri-tert-butylphosphine (e.g., in a 1:1 molar ratio when X is Br, and in a 1:2 molar ratio when X is Cl), the solvent is tetrahydrofuran when X is Br and dioxane when X is Cl, and the reaction mixture contains zinc dust. In Tables 1 and 2: t means tertiary, s means secondary, n means normal, i means iso, c means cyclo, Me means methyl, Et means ethyl, Pr means propyl, and Bu means butyl. Concatenations of groups are abbreviated similarly; for example, "c-$PrCH_2$" means cyclopropylmethyl

TABLE 1

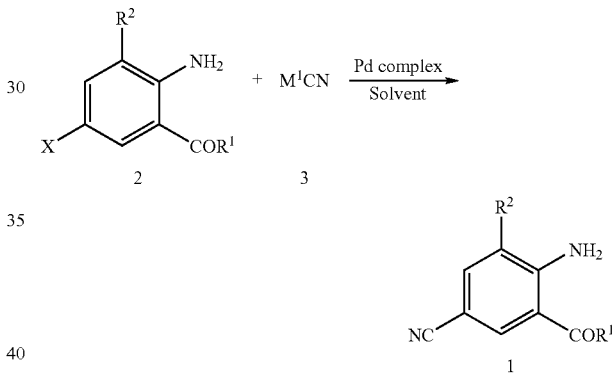

| $R^1$ is $NHR^3$. X is Br and $M^1$ is Na. | | $R^1$ is $NHR^3$. X is Cl and $M^1$ is Na. | | $R^1$ is $NHR^3$. X is Br and $M^1$ is K. | |
|---|---|---|---|---|---|
| $R^2$ | $R^3$ | $R^2$ | $R^3$ | $R^2$ | $R^3$ |
| Me | H | Me | H | Me | H |
| Me | Me | Me | Me | Me | Me |
| Me | Et | Me | Et | Me | Et |
| Me | n-Pr | Me | n-Pr | Me | n-Pr |
| Me | i-Pr | Me | i-Pr | Me | i-Pr |
| Me | n-Bu | Me | n-Bu | Me | n-Bu |
| Me | i-Bu | Me | i-Bu | Me | i-Bu |
| Me | s-Bu | Me | s-Bu | Me | s-Bu |
| Me | t-Bu | Me | t-Bu | Me | t-Bu |
| Me | c-Pr | Me | c-Pr | Me | c-Pr |
| Me | c-$PrCH_2$ | Me | c-$PrCH_2$ | Me | c-$PrCH_2$ |
| Me | 1-$CH_3$-c-Pr | Me | 1-$CH_3$-c-Pr | Me | 1-$CH_3$-c-Pr |
| Me | 2-$CH_3$-c-Pr | Me | 2-$CH_3$-c-Pr | Me | 2-$CH_3$-c-Pr |

| $R^1$ is $NHR^3$. X is Cl and $M^1$ is K. | | $R^1$ is $NHR^3$. X is Cl and $M^1$ is K. | | $R^1$ is $NHR^3$. X is Cl and $M^1$ is K. | |
|---|---|---|---|---|---|
| $R^2$ | $R^3$ | $R^2$ | $R^3$ | $R^2$ | $R^3$ |
| Me | H | Me | n-Bu | Me | c-$PrCH_2$ |
| Me | Me | Me | i-Bu | Me | 1-$CH_3$-c-Pr |
| Me | Et | Me | s-Bu | Me | 2-$CH_3$-c-Pr |
| Me | n-Pr | Me | t-Bu | | |
| Me | i-Pr | Me | c-Pr | | |

TABLE 1-continued

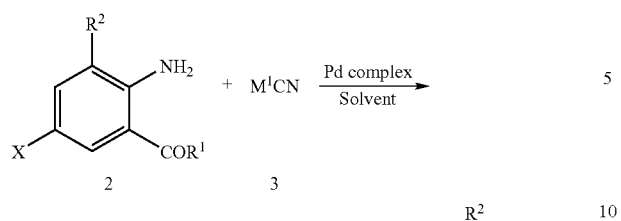

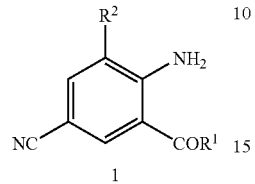

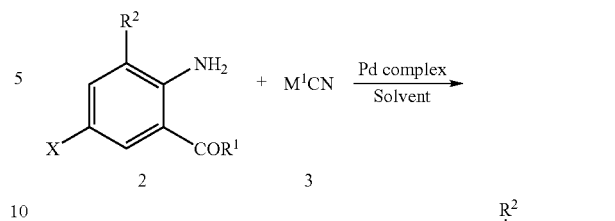

| R¹ is NHR³. X is Br and M¹ is Na. | | R¹ is NHR³. X is Br and M¹ is K. | |
|---|---|---|---|
| R² | R³ | R² | R³ |
| Cl | H | Cl | s-Bu |
| Cl | Me | Cl | t-Bu |
| Cl | Et | Cl | c-Pr |
| Cl | n-Pr | Cl | c-PrCH₂ |
| Cl | i-Pr | Cl | 1-CH₃-c-Pr |
| Cl | n-Bu | Cl | 2-CH₃-c-Pr |
| Cl | i-Bu | | |

| R² | R³ | R² | R³ |
|---|---|---|---|
| Cl | H | Cl | s-Bu |
| Cl | Me | Cl | t-Bu |
| Cl | Et | Cl | c-Pr |
| Cl | n-Pr | Cl | c-PrCH₂ |
| Cl | i-Pr | Cl | 1-CH₃-c-Pr |
| Cl | n-Bu | Cl | 2-CH₃-c-Pr |
| Cl | i-Bu | | |

| R¹ is OR⁴. X is Br and M¹ is Na. | | R¹ is OR⁴. X is Cl and M¹ is Na. | | R¹ is OR⁴. X is Br and M¹ is K. | |
|---|---|---|---|---|---|
| R² | R⁴ | R² | R⁴ | R² | R⁴ |
| Me | H | Me | H | Me | H |
| Me | Me | Me | Me | Me | Me |
| Me | Et | Me | Et | Me | Et |

| R¹ is OR⁴. X is Cl and M¹ is K. | | R¹ is OR⁴. X is Br and M¹ is Na. | | R¹ OR⁴. X is Br and M¹ is K | |
|---|---|---|---|---|---|
| R² | R⁴ | R² | R⁴ | R² | R⁴ |
| Me | H | Cl | H | Cl | H |
| Me | Me | Cl | Me | Cl | Me |
| Me | Et | Cl | Et | Cl | Et |

Table 2 illustrates particular transformations to prepare compounds of Formula 5 from compounds of Formulae 2 and 3 according to the method of the present invention. The conversion of the compound of Formula 2 to the compound of Formula 1 can be accomplished according to the method of Scheme 1 wherein R¹ is NHR³ using, for example, sodium cyanide (i.e. M¹ is Na), the palladium complex and solvent described for Table 1. The conversion of the compound of Formula 1 to the compound of Formula 5 can, for example, be accomplished according to the method of Scheme 6 using a sulfonyl chloride such as methanesulfonyl chloride in the presence of a solvent such as acetonitrile and a base such as 3-picoline.

TABLE 2

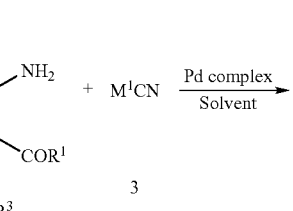

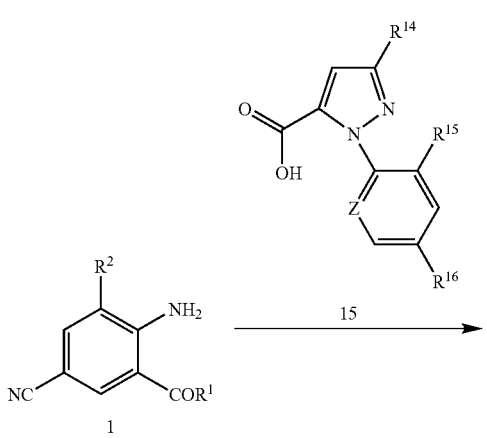

TABLE 2-continued

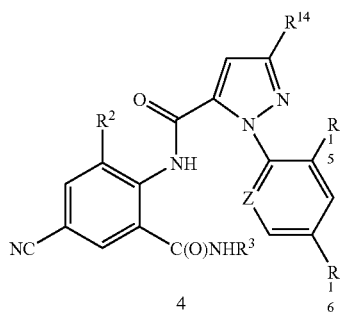

| R² is Me. X is Br. R¹⁶ is H and Z is N. | | | R² is Me. X is Br. R¹⁶ is H and Z is N. | | | R² is Me. X is Br. R¹⁶ is H and Z is N. | | |
|---|---|---|---|---|---|---|---|---|
| R³ | R¹⁴ | R¹⁵ | R³ | R¹⁴ | R¹⁵ | R³ | R¹⁴ | R¹⁵ |
| H | Br | F | H | Br | Cl | H | Br | Br |
| Me | Br | F | Me | Br | Cl | Me | Br | Br |
| Et | Br | F | Et | Br | Cl | Et | Br | Br |
| n-Pr | Br | F | n-Pr | Br | Cl | n-Pr | Br | Br |
| i-Pr | Br | F | i-Pr | Br | Cl | i-Pr | Br | Br |
| n-Bu | Br | F | n-Bu | Br | Cl | n-Bu | Br | Br |
| i-Bu | Br | F | i-Bu | Br | Cl | i-Bu | Br | Br |
| s-Bu | Br | F | s-Bu | Br | Cl | s-Bu | Br | Br |
| t-Bu | Br | F | t-Bu | Br | Cl | t-Bu | Br | Br |
| c-Pr | Br | F | c-Pr | Br | Cl | c-Pr | Br | Br |
| c-PrCH₂ | Br | F | c-PrCH₂ | Br | Cl | c-PrCH₂ | Br | Br |
| 1-CH₃-c-Pr | Br | F | 1-CH₃-c-Pr | Br | Cl | 1-CH₃-c-Pr | Br | Br |
| 2-CH₃-c-Pr | Br | F | 2-CH₃-c-Pr | Br | Cl | 2-CH₃-c-Pr | Br | Br |
| H | Cl | F | H | Cl | Cl | H | Cl | Br |
| Me | Cl | F | Me | Cl | Cl | Me | Cl | Br |
| Et | Cl | F | Et | Cl | Cl | Et | Cl | Br |
| n-Pr | Cl | F | n-Pr | Cl | Cl | n-Pr | Cl | Br |
| i-Pr | Cl | F | i-Pr | Cl | Cl | i-Pr | Cl | Br |
| n-Bu | Cl | F | n-Bu | Cl | Cl | n-Bu | Cl | Br |
| i-Bu | Cl | F | i-Bu | Cl | Cl | i-Bu | Cl | Br |
| s-Bu | Cl | F | s-Bu | Cl | Cl | s-Bu | Cl | Br |
| t-Bu | Cl | F | t-Bu | Cl | Cl | t-Bu | Cl | Br |
| c-Pr | Cl | F | c-Pr | Cl | Cl | c-Pr | Cl | Br |
| c-PrCH₂ | Cl | F | c-PrCH₂ | Cl | Cl | c-PrCH₂ | Cl | Br |
| 1-CH₃-c-Pr | Cl | F | 1-CH₃-c-Pr | Cl | Cl | 1-CH₃-c-Pr | Cl | Br |
| 2-CH₃-c-Pr | Cl | F | 2-CH₃-c-Pr | Cl | Cl | 2-CH₃-c-Pr | Cl | Br |
| H | OCH₂CF₃ | F | H | OCF₂H | F | H | CF₃ | Br |
| Me | OCH₂CF3 | F | Me | OCF₂H | F | Me | CF₃ | Br |
| t-Bu | OCH₂CF₃ | F | t-Bu | OCF₂H | F | t-Bu | CF₃ | Br |
| H | OCH₂CF₃ | Cl | H | OCF₂H | Cl | 1-CH₃-c-Pr | CF₃ | Br |
| Me | OCH₂CF₃ | Cl | Me | OCF₂H | Cl | 2-CH₃-c-Pr | CF₃ | Br |
| t-Bu | OCH₂CF₃ | Cl | t-Bu | OCF₂H | Cl | H | CF₃ | Cl |
| H | OCH₂CF₃ | Br | H | OCF₂H | Br | Me | CF₃ | Cl |
| Me | OCH₂CF₃ | Br | Me | OCF₂H | Br | t-Bu | CF₃ | Cl |
| t-Bu | OCH₂CF₃ | Br | t-Bu | OCF₂H | Br | 1-CH₃-c-Pr | CF₃ | Cl |
| H | CF₃ | F | t-Bu | CF₃ | F | 2-CH₃-c-Pr | CF₃ | Cl |
| Me | CF₃ | F | 1-CH₃-c-Pr | CF₃ | F | 2-CH₃-c-Pr | CF₃ | F |

| R² is Me. X is Cl. R¹⁶ is H and Z is N. | | | R² is Me. X is Cl. R¹⁶ is H and Z is N. | | | R² is Me. X is Cl. R¹⁶ is H and Z is N. | | |
|---|---|---|---|---|---|---|---|---|
| R³ | R¹⁴ | R¹⁵ | R³ | R¹⁴ | R¹⁵ | R³ | R¹⁴ | R¹⁵ |
| H | Br | F | H | Br | Cl | H | Br | Br |
| Me | Br | F | Me | Br | Cl | Me | Br | Br |
| Et | Br | F | Et | Br | Cl | Et | Br | Br |
| n-Pr | Br | F | n-Pr | Br | Cl | n-Pr | Br | Br |
| i-Pr | Br | F | i-Pr | Br | Cl | i-Pr | Br | Br |
| n-Bu | Br | F | n-Bu | Br | Cl | n-Bu | Br | Br |
| i-Bu | Br | F | i-Bu | Br | Cl | i-Bu | Br | Br |
| s-Bu | Br | F | s-Bu | Br | Cl | s-Bu | Br | Br |
| t-Bu | Br | F | t-Bu | Br | Cl | t-Bu | Br | Br |
| c-Pr | Br | F | c-Pr | Br | Cl | c-Pr | Br | Br |
| c-PrCH₂ | Br | F | c-PrCH₂ | Br | Cl | c-PrCH₂ | Br | Br |
| 1-CH₃-c-Pr | Br | F | 1-CH₃-c-Pr | Br | Cl | 1-CH₃-c-Pr | Br | Br |
| 2-CH₃-c-Pr | Br | F | 2-CH₃-c-Pr | Br | Cl | 2-CH₃-c-Pr | Br | Br |
| H | Cl | F | H | Cl | Cl | H | Cl | Br |

TABLE 2-continued

| R³ | R¹⁴ | R¹⁵ | R³ | R¹⁴ | R¹⁵ | R³ | R¹⁴ | R¹⁵ |
|---|---|---|---|---|---|---|---|---|
| Me | Cl | F | Me | Cl | Cl | Me | Cl | Br |
| Et | Cl | F | Et | Cl | Cl | Et | Cl | Br |
| n-Pr | Cl | F | n-Pr | Cl | Cl | n-Pr | Cl | Br |
| i-Pr | Cl | F | i-Pr | Cl | Cl | i-Pr | Cl | Br |
| n-Bu | Cl | F | n-Bu | Cl | Cl | n-Bu | Cl | Br |
| i-Bu | Cl | F | i-Bu | Cl | Cl | i-Bu | Cl | Br |
| s-Bu | Cl | F | s-Bu | Cl | Cl | s-Bu | Cl | Br |
| t-Bu | Cl | F | t-Bu | Cl | Cl | t-Bu | Cl | Br |
| c-Pr | Cl | F | c-Pr | Cl | Cl | c-Pr | Cl | Br |
| c-PrCH₂ | Cl | F | c-PrCH₂ | Cl | Cl | c-PrCH₂ | Cl | Br |
| 1-CH₃-c-Pr | Cl | F | 1-CH₃-c-Pr | Cl | Cl | 1-CH₃-c-Pr | Cl | Br |
| 2-CH₃-c-Pr | Cl | F | 2-CH₃-c-Pr | Cl | Cl | 2-CH₃-c-Pr | Cl | Br |
| H | OCH₂CF₃ | F | H | OCF₂H | F | H | CF₃ | Br |
| Me | OCH₂CF₃ | F | Me | OCF₂H | F | Me | CF₃ | Br |
| t-Bu | OCH₂CF₃ | F | t-Bu | OCF₂H | F | t-Bu | CF₃ | Br |
| H | OCH₂CF₃ | Cl | H | OCF₂H | Cl | 1-CH₃-c-Pr | CF₃ | Br |
| Me | OCH₂CF₃ | Cl | Me | OCF₂H | Cl | 2-CH₃-c-Pr | CF₃ | Br |
| t-Bu | OCH₂CF₃ | Cl | t-Bu | OCF₂H | Cl | H | CF₃ | Cl |
| H | OCH₂CF₃ | Br | H | OCF₂H | Br | Me | CF₃ | Cl |
| Me | OCH₂CF₃ | Br | Me | OCF₂H | Br | t-Bu | CF₃ | Cl |
| t-Bu | OCH₂CF₃ | Br | t-Bu | OCF₂H | Br | 1-CH₃-c-Pr | CF₃ | Cl |
| H | CF₃ | F | t-Bu | CF₃ | F | 2-CH₃-c-Pr | CF₃ | Cl |
| Me | CF₃ | F | 1-CH₃-c-Pr | CF₃ | F | 2-CH₃-c-Pr | CF₃ | F |

| R² is Cl, X is Br, R¹⁶ is H and Z is N. | | | R² is Cl, X is Br, R¹⁶ is H and Z is N. | | | R² is Cl, X is Br, R¹⁶ is H and Z is N. | | |
|---|---|---|---|---|---|---|---|---|
| R³ | R¹⁴ | R¹⁵ | R³ | R¹⁴ | R¹⁵ | R³ | R¹⁴ | R¹⁵ |
| H | Br | F | H | Br | Cl | H | Br | Br |
| Me | Br | F | Me | Br | Cl | Me | Br | Br |
| Et | Br | F | Et | Br | Cl | Et | Br | Br |
| n-Pr | Br | F | n-Pr | Br | Cl | n-Pr | Br | Br |
| i-Pr | Br | F | i-Pr | Br | Cl | i-Pr | Br | Br |
| n-Bu | Br | F | n-Bu | Br | Cl | n-Bu | Br | Br |
| i-Bu | Br | F | i-Bu | Br | Cl | i-Bu | Br | Br |
| s-Bu | Br | F | s-Bu | Br | Cl | s-Bu | Br | Br |
| t-Bu | Br | F | t-Bu | Br | Cl | t-Bu | Br | Br |
| c-Pr | Br | F | c-Pr | Br | Cl | c-Pr | Br | Br |
| c-PrCH₂ | Br | F | c-PrCH₂ | Br | Cl | c-PrCH₂ | Br | Br |
| 1-CH₃-c-Pr | Br | F | 1-CH₃-c-Pr | Br | Cl | 1-CH₃-c-Pr | Br | Br |
| 2-CH₃-c-Pr | Br | F | 2-CH₃-c-Pr | Br | Cl | 2-CH₃-c-Pr | Br | Br |
| H | Cl | F | H | Cl | Cl | H | Cl | Br |
| Me | Cl | F | Me | Cl | Cl | Me | Cl | Br |
| Et | Cl | F | Et | Cl | Cl | Et | Cl | Br |
| n-Pr | Cl | F | n-Pr | Cl | Cl | n-Pr | Cl | Br |
| i-Pr | Cl | F | i-Pr | Cl | Cl | i-Pr | Cl | Br |
| n-Bu | Cl | F | n-Bu | Cl | Cl | n-Bu | Cl | Br |
| i-Bu | Cl | F | i-Bu | Cl | Cl | i-Bu | Cl | Br |
| s-Bu | Cl | F | s-Bu | Cl | Cl | s-Bu | Cl | Br |
| t-Bu | Cl | F | t-Bu | Cl | Cl | t-Bu | Cl | Br |
| c-Pr | Cl | F | c-Pr | Cl | Cl | c-Pr | Cl | Br |
| c-PrCH₂ | Cl | F | c-PrCH₂ | Cl | Cl | c-PrCH₂ | Cl | Br |
| 1-CH₃-c-Pr | Cl | F | 1-CH₃-c-Pr | Cl | Cl | 1-CH₃-c-Pr | Cl | Br |
| 2-CH₃-c-Pr | Cl | F | 2-CH₃-c-Pr | Cl | Cl | 2-CH₃-c-Pr | Cl | Br |
| H | OCH₂CF₃ | F | H | OCF₂H | F | H | CF₃ | Br |
| Me | OCH₂CF₃ | F | Me | OCF₂H | F | Me | CF₃ | Br |
| t-Bu | OCH₂CF₃ | F | t-Bu | OCF₂H | F | t-Bu | CF₃ | Br |
| H | OCH₂CF₃ | Cl | H | OCF₂H | Cl | 1-CH₃-c-Pr | CF₃ | Br |
| Me | OCH₂CF₃ | Cl | Me | OCF₂H | Cl | 2-CH₃-c-Pr | CF₃ | Br |
| t-Bu | OCH₂CF₃ | Cl | t-Bu | OCF₂H | Cl | H | CF₃ | Cl |
| H | OCH₂CF₃ | Br | H | OCF₂H | Br | Me | CF₃ | Cl |
| Me | OCH₂CF₃ | Br | Me | OCF₂H | Br | t-Bu | CF₃ | Cl |
| t-Bu | OCH₂CF₃ | Br | t-Bu | OCF₂H | Br | 1-CH₃-c-Pr | CF₃ | Cl |
| H | CF₃ | F | t-Bu | CF₃ | F | 2-CH₃-c-Pr | CF₃ | Cl |
| Me | CF₃ | F | 1-CH₃-c-Pr | CF₃ | F | 2-CH₃-c-Pr | CF₃ | F |

| R² is Me, X is Br, R¹⁶ is H and Z is CH. | | | R² is Me, X is Br, R¹⁶ is H and Z is CH. | | | R² is Me, X is Br, R¹⁶ is H and Z is CH. | | |
|---|---|---|---|---|---|---|---|---|
| R³ | R¹⁴ | R¹⁵ | R³ | R¹⁴ | R¹⁵ | R³ | R¹⁴ | R¹⁵ |
| H | Br | F | Me | OCF₂H | F | H | Br | Br |
| Me | Br | F | Et | OCF₂H | F | Me | Br | Br |
| t-Bu | Br | F | c-PrCH₂ | OCF₂H | F | t-Bu | Br | Br |
| c-Pr | Br | F | c-Pr | OCF₂H | Cl | c-Pr | Br | Br |
| c-PrCH₂ | Br | F | c-PrCH₂ | OCF₂H | Cl | c-PrCH₂ | Br | Br |
| H | Cl | F | Me | OCF₂H | Br | H | Cl | Cl |

TABLE 2-continued

| $R^3$ | $R^{14}$ | $R^{15}$ | $R^3$ | $R^{14}$ | $R^{15}$ | $R^3$ | $R^{14}$ | $R^{15}$ |
|---|---|---|---|---|---|---|---|---|
| Me | Cl | F | Et | OCF$_2$H | Br | Me | Cl | Cl |
| t-Bu | Cl | F | Me | OCH$_2$CF$_3$ | F | t-Bu | Cl | Cl |
| c-Pr | Cl | F | Et | OCH$_2$CF$_3$ | F | c-Pr | Cl | Cl |
| c-PrCH$_2$ | Cl | F | c-Pr | OCH$_2$CF$_3$ | F | c-PrCH$_2$ | Cl | Cl |
| H | Cl | Br | c-PrCH$_2$ | OCH$_2$CF$_3$ | Cl | Et | CF$_3$ | Br |
| Me | Cl | Br | Me | OCH$_2$CF$_3$ | Br | c-Pr | CF$_3$ | Br |
| t-Bu | Cl | Br | Et | OCH$_2$CF$_3$ | Br | c-PrCH$_2$ | CF$_3$ | Br |
| c-Pr | Cl | Br | H | Br | Cl | H | CF$_3$ | Cl |
| c-PrCH$_2$ | Cl | Br | Me | Br | Cl | Me | CF$_3$ | Cl |
| H | CF$_3$ | F | i-Bu | Br | Cl | t-Bu | CF$_3$ | Cl |
| Me | CF$_3$ | F | c-Pr | Br | Cl | Me | CF$_3$ | Cl |
| t-Bu | CF$_3$ | F | c-PrCH$_2$ | Br | Cl | 2-CH$_3$-c-Pr | CF$_3$ | F |

| $R^2$ is Me. X is Cl. $R^{16}$ is H and Z is CH. | | | $R^2$ is Me. X is Cl. $R^{16}$ is H and Z is CH. | | | $R^2$ is Me. X is Cl. $R^{16}$ is H and Z is CH. | | |
|---|---|---|---|---|---|---|---|---|
| $R^3$ | $R^{14}$ | $R^{15}$ | $R^3$ | $R^{14}$ | $R^{15}$ | $R^3$ | $R^{14}$ | $R^{15}$ |
| H | Br | F | Me | OCF$_2$H | F | H | Br | Br |
| Me | Br | F | Et | OCF$_2$H | F | Me | Br | Br |
| t-Bu | Br | F | c-PrCH$_2$ | OCF$_2$H | F | t-Bu | Br | Br |
| c-Pr | Br | F | c-Pr | OCF$_2$H | Cl | c-Pr | Br | Br |
| c-PrCH$_2$ | Br | F | c-PrCH$_2$ | OCF$_2$H | Cl | c-PrCH$_2$ | Br | Br |
| H | Cl | F | Me | OCF$_2$H | Br | H | Cl | Cl |
| Me | Cl | F | Et | OCF$_2$H | Br | Me | Cl | Cl |
| t-Bu | Cl | F | Me | OCH$_2$CF$_3$ | F | t-Bu | Cl | Cl |
| c-Pr | Cl | F | Et | OCH$_2$CF$_3$ | F | c-Pr | Cl | Cl |
| c-PrCH$_2$ | Cl | F | c-Pr | OCH$_2$CF$_3$ | F | c-PrCH$_2$ | Cl | Cl |
| H | Cl | Br | c-PrCH$_2$ | OCH$_2$CF$_3$ | Cl | Et | CF$_3$ | Br |
| Me | Cl | Br | Me | OCH$_2$CF$_3$ | Br | c-Pr | CF$_3$ | Br |
| t-Bu | Cl | Br | Et | OCH$_2$CF$_3$ | Br | c-PrCH$_2$ | CF$_3$ | Br |
| c-Pr | Cl | Br | H | Br | Cl | H | CF$_3$ | Cl |
| c-PrCH$_2$ | Cl | Br | Me | Br | Cl | Me | CF$_3$ | Cl |
| H | CF$_3$ | F | i-Bu | Br | Cl | t-Bu | CF$_3$ | Cl |
| Me | CF$_3$ | F | c-Pr | Br | Cl | Me | CF$_3$ | Cl |
| t-Bu | CF$_3$ | F | c-PrCH$_2$ | Br | Cl | 2-CH$_3$-c-Pr | CF$_3$ | F |

| $R^2$ is Cl. X is Br. $R^{16}$ is H and Z is CH. | | | $R^2$ is Cl. X is Br. $R^{16}$ is H and Z is CH. | | | $R^2$ is Cl. X is Br. $R^{16}$ is H and Z is CH. | | |
|---|---|---|---|---|---|---|---|---|
| $R^3$ | $R^{14}$ | $R^{15}$ | $R^3$ | $R^{14}$ | $R^{15}$ | $R^3$ | $R^{14}$ | $R^{15}$ |
| H | Br | F | Me | OCF$_2$H | F | H | Br | Br |
| Me | Br | F | Et | OCF$_2$H | F | Me | Br | Br |
| t-Bu | Br | F | c-PrCH$_2$ | OCF$_2$H | F | t-Bu | Br | Br |
| c-Pr | Br | F | c-Pr | OCF$_2$H | Cl | c-Pr | Br | Br |
| c-PrCH$_2$ | Br | F | c-PrCH$_2$ | OCF$_2$H | Cl | c-PrCH$_2$ | Br | Br |
| H | Cl | F | Me | OCF$_2$H | Br | H | Cl | Cl |
| Me | Cl | F | Et | OCF$_2$H | Br | Me | Cl | Cl |
| t-Bu | Cl | F | Me | OCH$_2$CF$_3$ | F | i-Bu | Cl | Cl |
| c-Pr | Cl | F | Et | OCH$_2$CF$_3$ | F | c-Pr | Cl | Cl |
| c-PrCH$_2$ | Cl | F | c-Pr | OCH$_2$CF$_3$ | F | c-PrCH$_2$ | Cl | Cl |
| H | Cl | Br | c-PrCH$_2$ | OCH$_2$CF$_3$ | Cl | Et | CF$_3$ | Br |
| Me | Cl | Br | Me | OCH$_2$CF$_3$ | Br | c-Pr | CF$_3$ | Br |
| t-Bu | Cl | Br | Et | OCH$_2$CF$_3$ | Br | c-PrCH$_2$ | CF$_3$ | Br |
| c-Pr | Cl | Br | H | Br | Cl | H | CF$_3$ | Cl |
| c-PrCH$_2$ | Cl | Br | Me | Br | Cl | Me | CF$_3$ | Cl |
| H | CF$_3$ | F | t-Bu | Br | Cl | t-Bu | CF$_3$ | Cl |
| Me | CF$_3$ | F | c-Pr | Br | Cl | Me | CF$_3$ | Cl |
| t-Bu | CF$_3$ | F | c-PrCH$_2$ | Br | Cl | 2-CH$_3$-c-Pr | CF$_3$ | F |

| $R^2$ is Me. X is Br. $R^{16}$ is F and Z is N. | | | $R^2$ is Me. X is Br. $R^{16}$ is F and Z is N. | | | $R^2$ is Me. X is Br. $R^{16}$ is F and Z is N. | | |
|---|---|---|---|---|---|---|---|---|
| $R^3$ | $R^{14}$ | $R^{15}$ | $R^3$ | $R^{14}$ | $R^{15}$ | $R^3$ | $R^{14}$ | $R^{15}$ |
| H | Br | F | H | Cl | Cl | H | Br | Br |
| Me | Br | F | Me | Cl | Cl | Me | Br | Br |
| t-Bu | Br | F | t-Bu | Cl | Cl | t-Bu | Br | Br |
| c-Pr | Br | F | c-Pr | Cl | Cl | c-Pr | Br | Br |
| c-PrCH$_2$ | Br | F | c-PrCH$_2$ | Cl | Cl | c-PrCH$_2$ | Br | Br |
| H | Cl | F | Me | OCF$_2$H | F | H | Cl | Br |
| Me | Cl | F | Et | OCF$_2$H | F | Me | Cl | Br |
| t-Bu | Cl | F | c-Pr | OCF$_2$H | Cl | t-Bu | Cl | Br |
| c-Pr | Cl | F | c-PrCH$_2$ | OCF$_2$H | Cl | c-Pr | Cl | Br |
| c-PrCH$_2$ | Cl | F | Me | OCF$_2$H | Br | c-PrCH$_2$ | Cl | Br |
| H | Br | Cl | Et | OCF$_2$H | Br | H | CF$_3$ | F |

TABLE 2-continued

| R³ | R¹⁴ | R¹⁵ | R³ | R¹⁴ | R¹⁵ | R³ | R¹⁴ | R¹⁵ |
|---|---|---|---|---|---|---|---|---|
| Me | Br | Cl | Me | OCH₂CF₃ | F | Me | CF₃ | F |
| t-Bu | Br | Cl | Et | OCH₂CF₃ | F | t-Bu | CF₃ | F |
| c-Pr | Br | Cl | c-Pr | OCH₂CF₃ | Cl | 2-CH₃-c-Pr | CF₃ | F |
| c-PrCH₂ | Br | Cl | c-PrCH₂ | OCH₂CF₃ | Cl | Et | CF₃ | Br |
| H | CF₃ | Cl | Me | OCH₂CF₃ | Br | c-Pr | CF₃ | Br |
| Me | CF₃ | Cl | F | OCH₂CF₃ | Br | c-PrCH₂ | CF₃ | Br |
| t-Bu | CF₃ | Cl | Me | CF₃ | Br | | | |

| R² is Me. X is Cl. R¹⁶ is F and Z is N. | | | R² is Me. X is Cl. R¹⁶ is F and Z is N. | | | R² is Me. X is Cl. R¹⁶ is F and Z is N. | | |
|---|---|---|---|---|---|---|---|---|
| H | Br | F | H | Cl | Cl | H | Br | Br |
| Me | Br | F | Me | Cl | Cl | Me | Br | Br |
| t-Bu | Br | F | t-Bu | Cl | Cl | t-Bu | Br | Br |
| c-Pr | Br | F | c-Pr | Cl | Cl | c-Pr | Br | Br |
| c-PrCH₂ | Br | F | c-PrCH₂ | Cl | Cl | c-PrCH₂ | Br | Br |
| H | Cl | F | Me | OCF₂H | F | H | Cl | Br |
| Me | Cl | F | Et | OCF₂H | F | Me | Cl | Br |
| t-Bu | Cl | F | c-Pr | OCF₂H | Cl | t-Bu | Cl | Br |
| c-Pr | Cl | F | c-PrCH₂ | OCF₂H | Cl | c-Pr | Cl | Br |
| c-PrCH₂ | Cl | F | Me | OCF₂H | Br | c-PrCH₂ | Cl | Br |
| H | Br | Cl | Et | OCF₂H | Br | H | CF₃ | F |
| Me | Br | Cl | Me | OCH₂CF₃ | F | Me | CF₃ | F |
| t-Bu | Br | Cl | Et | OCH₂CF₃ | F | t-Bu | CF₃ | F |
| c-Pr | Br | Cl | c-Pr | OCH₂CF₃ | Cl | 2-CH₃c-Pr | CF₃ | F |
| c-PrCH₂ | Br | Cl | c-PrCH₂ | OCH₂CF₃ | Cl | Et | CF₃ | Br |
| H | CF₃ | Cl | Me | OCH₂CF₃ | Br | c-Pr | CF₃ | Br |
| Me | CF₃ | Cl | Me | OCH₂CF₃ | Br | c-PrCH₂ | CF₃ | Br |
| t-Bu | CF₃ | Cl | Me | CF₃ | Br | | | |

| R² is Cl. X is Br. R¹⁶ is F and Z is N. | | | R² is Cl. X is Br. R¹⁶ is F and Z is N. | | | R² is Cl. X is Br. R¹⁶ is F and Z is N. | | |
|---|---|---|---|---|---|---|---|---|
| R³ | R¹⁴ | R¹⁵ | R³ | R¹⁴ | R¹⁵ | R³ | R¹⁴ | R¹⁵ |
| H | Br | F | H | Cl | Cl | H | Br | Br |
| Me | Br | F | Me | Cl | Cl | Me | Br | Br |
| t-Bu | Br | F | t-Bu | Cl | Cl | t-Bu | Br | Br |
| c-Pr | Br | F | c-Pr | Cl | Cl | c-Pr | Br | Br |
| c-PrCH₂ | Br | F | c-PrCH₂ | Cl | Cl | c-PrCH₂ | Br | Br |
| H | Cl | F | Me | OCF₂H | F | H | Cl | Br |
| Me | Cl | F | Et | OCF₂H | F | Me | Cl | Br |
| t-Bu | Cl | F | c-Pr | OCF₂H | Cl | t-Bu | Cl | Br |
| c-Pr | Cl | F | c-PrCH₂ | OCF₂H | Cl | c-Pr | Cl | Br |
| c-PrCH₂ | Cl | F | Me | OCF₂H | Br | c-PrCH₂ | Cl | Br |
| H | Br | Cl | Et | OCF₂H | Br | H | CF₃ | F |
| Me | Br | Cl | Me | OCH₂CF₃ | F | Me | CF₃ | F |
| t-Bu | Br | Cl | Et | OCH₂CF₃ | F | t-Bu | CF₃ | F |
| c-Pr | Br | Cl | c-Pr | OCH₂CF₃ | Cl | 2-CH₃-c-Pr | CF₃ | F |
| c-PrCH₂ | Br | Cl | c-PrCH₂ | OCH,CF₃ | Cl | Et | CF₃ | Br |
| H | CF₃ | Cl | Me | OCH₂CF₃ | Br | c-Pr | CF₃ | Br |
| Me | CF₃ | Cl | Et | OCH₂CF₃ | Br | c-PrCH₂ | CF₃ | Br |
| t-Bu | CF₃ | Cl | Me | CF₃ | Br | | | |

| R² is Me. X is Br. R¹⁶ is Cl and Z is N. | | | R² is Me. X is Br. R¹⁶ is Cl and Z is N. | | | R² is Me. X is Br. R¹⁶ is Cl and Z is N. | | |
|---|---|---|---|---|---|---|---|---|
| R³ | R¹⁴ | R¹⁵ | R³ | R¹⁴ | R¹⁵ | R³ | R¹⁴ | R¹⁵ |
| H | Br | F | H | Cl | Cl | H | Br | Br |
| Me | Br | F | Me | Cl | Cl | Me | Br | Br |
| t-Bu | Br | F | t-Bu | Cl | Cl | t-Bu | Br | Br |
| c-Pr | Br | F | c-Pr | Cl | Cl | c-Pr | Br | Br |
| c-PrCH₂ | Br | F | c-PrCH₂ | Cl | Cl | c-PrCH₂ | Br | Br |
| H | Cl | F | Me | OCH₂CF₃ | F | H | Cl | Br |
| Me | Cl | F | Et | OCH₂CF₃ | F | Me | Cl | Br |
| t-Bu | Cl | F | c-Pr | OCH₂CF₃ | Cl | t-Bu | Cl | Br |
| c-Pr | Cl | F | c-PrCH₂ | OCH₂CF₃ | Cl | c-Pr | Cl | Br |
| c-PrCH₂ | Cl | F | Me | OCH₂CF₃ | Br | c-PrCH₂ | Cl | Br |
| H | Br | Cl | Et | OCH₂CF₃ | Br | H | CF₃ | Cl |
| Me | Br | Cl | Me | OCF₂H | F | Me | CF₃ | Cl |
| t-Bu | Br | Cl | Et | OCF₂H | F | t-Bu | CF₃ | Cl |
| c-Pr | Br | Cl | c-Pr | OCF₂H | Cl | Me | CF₃ | Br |
| c-PrCH₂ | Br | Cl | c-PrCH₂ | OCF₂H | Cl | Et | CF₃ | Br |
| H | CF₃ | F | Me | OCF₂H | Br | c-Pr | CF₃ | Br |

TABLE 2-continued

| Me | CF$_3$ | F | Et | OCF$_2$H | Br | c-PrCH$_2$ | CF$_3$ | Br |
| t-Bu | CF$_3$ | F | 2-CH$_3$-c-Pr | CF$_3$ | F | | | |

| R$^2$ is Me. X is Cl. R$^{16}$ is Cl and Z is N. | | | R$^2$ is Me. X is Cl. R$^{16}$ is Cl and Z is N. | | | R$^2$ is Me. X is Cl. R$^{16}$ is Cl and Z is N. | | |
|---|---|---|---|---|---|---|---|---|
| R$^3$ | R$^{14}$ | R$^{15}$ | R$^3$ | R$^{14}$ | R$^{15}$ | R$^3$ | R$^{14}$ | R$^{15}$ |
| H | Br | F | H | Cl | Cl | H | Br | Br |
| Me | Br | F | Me | Cl | Cl | Me | Br | Br |
| t-Bu | Br | F | t-Bu | Cl | Cl | t-Bu | Br | Br |
| c-Pr | Br | F | c-Pr | Cl | Cl | c-Pr | Br | Br |
| c-PrCH$_2$ | Br | F | c-PrCH$_2$ | Cl | Cl | c-PrCH$_2$ | Br | Br |
| H | Cl | F | Me | OCH$_2$CF$_3$ | F | H | Cl | Br |
| Me | Cl | F | Et | OCH$_2$CF$_3$ | F | Me | Cl | Br |
| t-Bu | Cl | F | c-Pr | OCH$_2$CF$_3$ | Cl | t-Bu | Cl | Br |
| c-Pr | Cl | F | c-PrCH$_2$ | OCH$_2$CF$_3$ | Cl | c-Pr | Cl | Br |
| c-PrCH$_2$ | Cl | F | Me | OCH$_2$CF$_3$ | Br | c-PrCH$_2$ | Cl | Br |
| H | Br | Cl | Et | OCH$_2$CF$_3$ | Br | H | CF$_3$ | Cl |
| Me | Br | Cl | Me | OCF$_2$H | F | Me | CF$_3$ | Cl |
| t-Bu | Br | Cl | Et | OCF$_2$H | F | t-Bu | CF$_3$ | Cl |
| c-Pr | Br | Cl | c-Pr | OCF$_2$H | Cl | Me | CF$_3$ | Br |
| c-PrCH$_2$ | Br | Cl | c-PrCH$_2$ | OCF$_2$H | Cl | Et | CF$_3$ | Br |
| H | CF$_3$ | F | Me | OCF$_2$H | Br | c-Pr | CF$_3$ | Br |
| Me | CF$_3$ | F | Et | OCF$_2$H | Br | c-PrCH$_2$ | CF$_3$ | Br |
| t-Bu | CF$_3$ | F | 2-CH$_3$-c-Pr | CF$_3$ | F | | | |

| R$^2$ is Cl. X is Br. R$^{16}$ is Cl and Z is N. | | | R$^2$ is Me. X is Br. R$^{16}$ is Cl and Z is N. | | | R$^2$ is Me. X is Br. R$^{16}$ is Cl and Z is N. | | |
|---|---|---|---|---|---|---|---|---|
| R$^3$ | R$^{14}$ | R$^{15}$ | R$^3$ | R$^{14}$ | R$^{15}$ | R$^3$ | R$^{14}$ | R$^{15}$ |
| H | Br | F | H | Cl | Cl | H | Br | Br |
| Me | Br | F | Me | Cl | Cl | Me | Br | Br |
| t-Bu | Br | F | t-Bu | Cl | Cl | t-Bu | Br | Br |
| c-Pr | Br | F | c-Pr | Cl | Cl | c-Pr | Br | Br |
| c-PrCH$_2$ | Br | F | c-PrCH$_2$ | Cl | Cl | c-PrCH$_2$ | Br | Br |
| H | Cl | F | Me | OCH$_2$CF$_3$ | F | H | Cl | Br |
| Me | Cl | F | Et | OCH$_2$CF$_3$ | F | Me | Cl | Br |
| t-Bu | Cl | F | c-Pr | OCH$_2$CF$_3$ | Cl | t-Bu | Cl | Br |
| c-Pr | Cl | F | c-PrCH$_2$ | OCH$_2$CF$_3$ | Cl | c-Pr | Cl | Br |
| c-PrCH$_2$ | Cl | F | Me | OCH$_2$CF$_3$ | Br | c-PrCH$_2$ | Cl | Br |
| H | Br | Cl | Et | OCH$_2$CF$_3$ | Br | H | CF$_3$ | Cl |
| Me | Br | Cl | Me | OCF$_2$H | F | Me | CF$_3$ | Cl |
| t-Bu | Br | Cl | Et | OCF$_2$H | F | t-Bu | CF$_3$ | Cl |
| c-Pr | Br | Cl | c-Pr | OCF$_2$H | Cl | Me | CF$_3$ | Br |
| c-PrCH$_2$ | Br | Cl | c-PrCH$_2$ | OCF$_2$H | Cl | Et | CF$_3$ | Br |
| H | CF$_3$ | F | Me | OCF$_2$H | Br | c-Pr | CF$_3$ | Br |
| Me | CF$_3$ | F | Et | OCF$_2$H | Br | c-PrCH$_2$ | CF$_3$ | Br |
| t-Bu | CF$_3$ | F | 2-CH$_3$-c-Pr | CF$_3$ | F | | | |

What is claimed is:

1. A method for preparing a compound of Formula 1

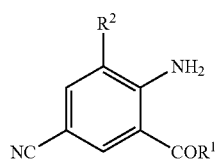

wherein
 R$^1$ is NHR$^3$ or OR$^4$;
 R$^2$ is Cl or CH$_3$;
 R$^3$ is H, C$_1$-C$_4$ alkyl, cyclopropyl, cyclopropylmethyl or methylcyclopropyl; and
 R$^4$ is H or C$_1$-C$_4$ alkyl;

comprising contacting (1) a compound of Formula 2

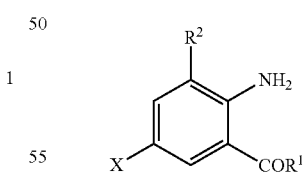

wherein X is Br or Cl;
with (2) at least one compound of Formula 3

$$M^1CN \qquad 3$$

wherein M$^1$ is an alkali metal
in the presence of (3) a solvent comprising one or more organic solvents selected from ethers and nitriles; and (4) a catalytically effective amount of a palladium complex comprising at least one tertiary phosphine ligand selected from the group consisting of benzyl-di-1-adamantylphosphine, di-tert-butylneopentylphosphine or tri-tert-butylphosphine;
provided that when $R^2$ is Cl, then X is Br; and when X is Cl, then the tertiary phosphine ligand is tri-tert-butylphosphine.

2. The method of claim 1 wherein the palladium complex is generated in situ.

3. The method of claim 1 wherein the palladium is complexed with tri-tert-butylphosphine.

4. The method of claim 1 wherein the solvent comprises one or more organic solvents selected from the group consisting of tetrahydrofuran, dioxane and acetonitrile.

5. The method of claim 1 wherein the solvent comprises a crown ether.

6. The method of claim 1 wherein the compound of Formula 2, the at least one compound of Formula 3, the palladium complex and the solvent are contacted at a temperature between about 0 and about 140° C.

7. The method of claim 6 wherein the compound of Formula 2, the at least one compound of Formula 3, the palladium catalyst and the solvent are contacted at a temperature between about 20 and about 100° C.

8. The method of claim 1 wherein the compound of Formula 2, the at least one compound of Formula 3, the palladium catalyst and the solvent are contacted in the presence of a catalyst promoter.

9. The method of claim 1 wherein the compound of Formula 2, the at least one compound of Formula 3, the palladium catalyst and the solvent are contacted in the presence of zinc metal.

10. The method of claim 1 wherein $R^1$ is $NHR^3$.

11. The method of claim 1 wherein $R^3$ is $C_1$-$C_4$ alkyl or cyclopropylmethyl.

12. The method of claim 11 wherein $R^3$ is methyl.

13. The method of claim 1 wherein $R^2$ is methyl.

14. The method of claim 1 wherein $M^1$ is Na or K.

15. The method of claim 1 wherein $R^1$ is $NHR^3$, $R^2$ is methyl, $R^3$ is methyl, X is Br, $M^1$ is Na, the palladium complex comprises tri-tert-butylphosphine, and the solvent is tetrahydrofuran.

16. The method of claim 15 wherein the compound of Formula 2, the at least one compound of Formula 3, the palladium catalyst and the solvent are contacted in the presence of zinc metal.

17. The method of claim 1 wherein a solution of the palladium complex in a solvent comprising an ether is contacted with a mixture comprising the compound of Formula 2, at least one compound of Formula 3 and a nitrile solvent.

18. A method for preparing a compound of Formula 5

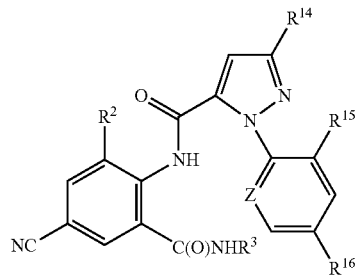

wherein
$R^2$ is Cl or $CH_3$;
$R^3$ is H, $C_1$-$C_4$ alkyl, cyclopropyl, cyclopropylmethyl, or methylcyclopropyl;
Z is $CR^{17}$ or N;
$R^{14}$ is Cl, Br, $CF_3$, $OCF_2H$ or $OCH_2CF_3$;
$R^{15}$ is F, Cl or Br;
$R^{16}$ is H, F or Cl; and
$R^{17}$ is H, F, Cl or Br;
using a compound of Formula 1

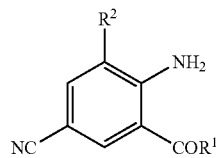

wherein
$R^1$ is $NHR^3$ or $OR^4$; and
$R^4$ is H or $C_1$-$C_4$ alkyl;
characterized by preparing said compound of Formula 1 by the method of claim 1.

19. The method of claim 18 wherein $R^1$ is $NHR^3$, $R^2$ is methyl, $R^3$ is methyl, $R^{14}$ is Br, $R^{15}$ is Cl, $R^{16}$ is H, and Z is N.

* * * * *